United States Patent
Xiang et al.

(10) Patent No.: US 9,376,431 B2
(45) Date of Patent: Jun. 28, 2016

(54) BIS-QUATERNARY CINCHONA ALKALOID SALTS AS ASYMMETRIC PHASE TRANSFER CATALYSTS

(71) Applicant: Merck Sharp & Dohme Corp., Rahway, NJ (US)

(72) Inventors: Bangping Xiang, Bridgewater, NJ (US); Nobuyoshi Yasuda, Mountainside, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/384,355

(22) PCT Filed: Mar. 13, 2013

(86) PCT No.: PCT/US2013/030688
§ 371 (c)(1),
(2) Date: Sep. 10, 2014

(87) PCT Pub. No.: WO2013/138413
PCT Pub. Date: Sep. 19, 2013

(65) Prior Publication Data
US 2015/0031891 A1    Jan. 29, 2015

Related U.S. Application Data

(60) Provisional application No. 61/610,746, filed on Mar. 14, 2012.

(51) Int. Cl.
C07D 453/04    (2006.01)
B01J 31/02    (2006.01)

(52) U.S. Cl.
CPC .......... *C07D 453/04* (2013.01); *B01J 31/0285* (2013.01); *B01J 2231/4205* (2013.01)

(58) Field of Classification Search
CPC .................................................. C07D 453/04
See application file for complete search history.

(56) References Cited

U.S. PATENT DOCUMENTS

| 6,313,247 | B1 | 11/2001 | Lindner et al. |
| 7,718,804 | B2 * | 5/2010 | Geddes .............. A61K 49/0021 546/13 |
| 8,338,602 | B2 * | 12/2012 | Geddes .............. A61K 49/0021 546/13 |
| 8,569,502 | B2 * | 10/2013 | Geddes .............. A61K 49/0021 546/102 |
| 9,174,989 | B2 | 11/2015 | Chen et al. |
| 2002/0115896 | A1 | 8/2002 | Pochapsky et al. |
| 2007/0020182 | A1 | 1/2007 | Geddes et al. |
| 2015/0038707 | A1 | 2/2015 | Belyk et al. |

FOREIGN PATENT DOCUMENTS

| EP | 0438796 | 7/1991 |
| EP | 2418190 | 2/2012 |
| WO | WO2011005731 | 1/2011 |

OTHER PUBLICATIONS

Babin, Bulletin de Societe de Parmacel de Bordeaux, 1974, 113(3), 101-106.*
Zeng, Chem Communications, vol. 46(14), 2435-2437, 2010.*
Babin, et. al., "Halogen derivatives of quinoliniums and isoquinoliniums" Bulletin de Societe de Pharmacel de Bordeaux, 1974, 113(3), 101-106.
Su, et al Theoretical investigation on mechanisim of asymmetric Michael addition or malanonitrile to chalcones catalyzed by Cinchona alkaloid aluminum III comple, Org. Biomol. Chem., 2011, 9, 6402.
Bangping Xiang, et al., "Discovery and Application of Doubly Quaternized Cinchona-Alkaloid-Based Phase-Transfer Catalysts". Angew Chem. Inl. Ed 2014, 53,8375-8378.
Ooi et al, Recent Advances in Asymmetric Phase Transfer Catalysis, Asymmetric Synthesis, 2007, vol. 36, pp. 4222-4266.
Yeboah et al, Recent Applications of Cinchona Alkaloids and their derivatives as catalysts in metal-free Asymmetric Synthesis, Tetrahedron, 2011, vol. 67, pp. 1725-1762.
Babin, English Translation, Bull Soc. Pharm Bordeaux, 1974, 113, pp. 101-106, that was prepared by Transperfect together with a certification from Transperfect for the translation.
U.S. Appl. No. 14/854,760, filed Sep. 15, 2015, Divisional Application of 9174989 issued Nov. 23, 2015.
Zeng, et al., Chem Comm, Highly Selective Recognition of Carbenicillin, Jan. 27, 2010, 2435-2437, 46(14).

* cited by examiner

*Primary Examiner* — D M Seaman
(74) *Attorney, Agent, or Firm* — John C. Todaro; H. Eric Fischer

(57) ABSTRACT

The invention is directed to novel bis-quarternary cinchona alkaloid salts and the use of bis-quarternary cinchona alkaloid salts in asymmetric phase transfer catalysis. The present invention is directed to novel bis-quarternary cinchona alkaloid salts and the use of bis-quarternary cinchona alkaloid salts in asymmetric phase transfer catalysis. On certain substrates and under specific reaction conditions, the inventors have discovered that the use of bis-quarternary cinchona alkaloid salts in asymmetric phase transfer catalysis surprisingly provides for a more active and efficient process as compared to mono-quarternary catalysts.

6 Claims, No Drawings

BIS-QUATERNARY CINCHONA ALKALOID SALTS AS ASYMMETRIC PHASE TRANSFER CATALYSTS

CROSS-REFERENCE TO RELATED APPLICATIONS

This application is a U.S. National Phase application under 35 U.S.C. §371 of PCT Application No. PCT/US2013/030688, filed Mar. 13, 2013, which application in turn claims the priority of U.S. Provisional Patent Application Ser. No. 60/610,746 filed Mar. 14, 2012.

BACKGROUND OF THE INVENTION

Cinchona alkaloid salts are known phase transfer catalysts useful in the asymmetric formation of carbon-carbon, carbon-heteroatom or carbon-halide bonds. See Takashi Ooi and Keiji Maruoka, *Recent Advances in Asymmetric Phase-Transfer Catalysis*, Angew. Chem. Int. Ed. 2007, 46, 4222-4266 ("Maruoka"). Maruoka reviews the various reactions in which phase-transfer catalysis is useful, including enantioselective alkylation, Michael addition, aldol and related reactions and Darzens reaction. Maruoka at page 4223 discusses the advantages of such phase transfer catalysis processes as involving "simple experimental procedures, mild reaction conditions, inexpensive and environmentally benign reagents and solvents and the possibility of conducting large-scale preparations." Thus, asymmetric phase transfer catalysis remains an important area for organic chemistry research.

The present invention is directed to novel bis-quarternary cinchona alkaloid salts and the use of bis-quarternary cinchona alkaloid salts in asymmetric phase transfer catalysis. On certain substrates and under specific reaction conditions, the inventors have discovered that the use of bis-quarternary cinchona alkaloid salts in asymmetric phase transfer catalysis surprisingly provides for a more active and efficient process as compared to mono-quarternary catalysts, providing high efficiency rates and asymmetric products in high enantiomeric excess.

SUMMARY OF THE INVENTION

The invention is directed to novel bis-quarternary cinchona alkaloid salts and the use of bis-quarternary cinchona alkaloid salts in asymmetric phase transfer catalysis.

DETAILED DESCRIPTION OF THE INVENTION

The invention encompasses bis-quarternary cinchona alkaloid salts having the chemical structure of Formula I:

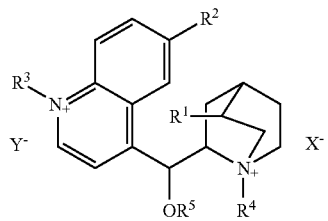

I wherein:
$R^1$ is selected from ethyl and vinyl,
$R^2$ is selected from hydrogen and methoxy,
$R^3$ and $R^4$ are independently selected from the grout, consisting of $C_{1-6}$alkyl, $C_{2-6}$alkenyl, $C_{2-6}$alkynyl, $C_{3-6}$ cycloalkyl, aryl, heteroaryl, —$C_{1-4}$alkyl-aryl and —$C_{1-4}$alkyl-heteroaryl, wherein $C_{1-6}$alkyl, $C_{2-6}$alkenyl, $C_{2-6}$alkynyl, $C_{3-6}$cycloalkyl, aryl, heteroaryl and the aryl and heteroaryl portions of —$C_{1-4}$alkyl-aryl and —$C_{1-4}$alkyl-heteroaryl are optionally substituted with one to five substituents independently selected from $R^6$,
$R^5$ is selected from the group consisting of hydrogen, C(O)R, C(O)OR, CONRR', and $C_{1-6}$alkyl,
$R^6$ is selected from the group consisting of $C_{1-4}$alkyl, $C_{1-4}$haloalkyl, aryl, $C_{1-4}$alkoxy, hydroxy, CN, $CO_2R$, CONRR', SR, $SO_2R$, $SO_3R$, $PR_2$, $PO(OR)_2$, PO(OR)(NRR'), PO(NRR')$_2$, P(OR)$_2$, P(OR)(NRR'), P(NRR')$_2$, SiRR'R", B(OR)$_2$, C(O)R, NRR', $NO_2$, and halogen,
each R, R' and R" is independently selected from the group consisting of, H, $C_{1-6}$alkyl, hydroxyl, $C_{1-6}$alkoxy, aryl, heteroaryl, —$CH_2$-aryl, —$CH_2$-heteroaryl, and
each X and Y are independently anions selected from halide, OH, $HSO_4$, $SO_4$, $BF_4$, $SbF_6$, carboxylate, carbonate, hydrogencarbonate, $NO_3$, sulfonate, hexafluorophosphate, phosphate, hydrogen phosphate and perchlorate, for use as phase transfer catalysts in the stereoselective formation of a carbon-carbon, carbon-heteroatom or carbon-halide bond on a substrate in a biphasic medium comprising an aqueous phase and organic phase or a micelle medium.

Unless depicted or specified otherwise, the cinchona alkaloid salts of Formula I encompass all stereoisomers, including cinchonine, cinchonidine, quinine, quinidine, dihydroquinidine, and dihydroquinine.

In an embodiment, the invention encompasses the bis-quarternary cinchona alkaloid salts of Formula I for use as phase transfer catalysts in one of the following asymmetric reactions: (1) alkylation with an electrophilic alkylating agent, (2) Michael addition with an electron deficient olefin, (3) aldol reaction with an aldehyde, (4) Mannich reaction with a α-imino ester, (5) Darzens reaction with an aldehyde, (6) Neber rearrangement of an oxime into an α-aminoketone, (7) epoxidation of an electron deficient olefin, (8) aziridination of an electron deficient olefin, (9) dihydroxylation of an electron deficient olefins, (10) fluorination of a carbonyl substrate, and (11) sulfenylation of a β-keto sulfoxide. The aforementioned reactions are well know in the art and described by Maruoka.

Another embodiment of the invention encompasses a process for stereoselectively producing a compound of Formula A

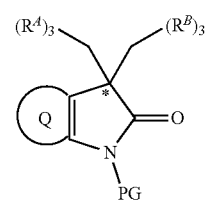

A wherein:
Q forms a fused 5- or 6-membered aromatic carbocyclic or heterocyclic ring, each optionally substituted with 1 to 4 $R^C$ groups,
each $R^A$ and each $R^B$ are independently hydrogen, halogen, hydroxy, amino or an organic substituent group, and one $R^A$ and one $R^B$ may be joined together to form a mono-, bi- or tricyclic carbocyclic or heterocyclic ring system, optionally substituted with 1 to 4 $R^C$ groups, $R^C$ is hydrogen, halogen, hydroxy, amino or an organic substituent group, PG is a nitrogen protecting group and

* represents an asymmetric center, comprising initiating a reaction of a compound of Formula B

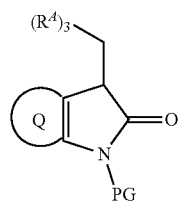

B with a compound of Formula C

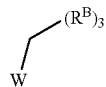

C wherein W is a functional group that has leaving ability, in a water-immiscible organic phase in the presence of a bis-quarternary cinchona alkaloid salt and a base in an aqueous phase to form a biphasic medium comprising the aqueous phase and water-immiscible organic phase, wherein the bis-quarternary cinchona alkaloid salt has the chemical structure of Formula I:

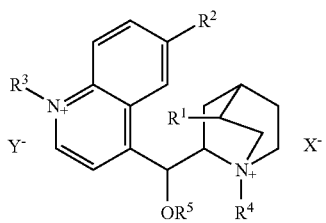

I wherein:

$R^1$ is selected from ethyl and vinyl, $R^2$ is selected from hydrogen and methoxy, $R^3$ and $R^4$ are independently selected from the group consisting of $C_{1-6}$alkyl, $C_{2-6}$alkenyl, $C_{2-6}$alkynyl, $C_{3-6}$cycloalkyl, aryl, heteroaryl, —$C_{1-4}$alkyl-aryl and —$C_{1-4}$alkyl-heteroaryl, wherein $C_{1-6}$alkyl, $C_{2-6}$alkenyl, $C_{2-6}$alkynyl, $C_{3-6}$cycloalkyl, aryl, heteroaryl and the aryl and heteroaryl portions of —$C_{1-4}$alkyl-aryl and —$C_{1-4}$alkyl-heteroaryl are optionally substituted with one to five substituents independently selected from $R^6$, $R^5$ is selected from the group consisting of hydrogen, C(O)R, C(O)OR, CONRR', and $C_{1-6}$alkyl, $R^6$ is selected from the group consisting of $C_{1-4}$alkyl, $C_{1-4}$haloalkyl, aryl, $C_{1-4}$alkoxy, hydroxy, CN, $CO_2R$, CONRR', SR, $SO_2R$, $SO_3R$, $PR_2$, $PO(OR)_2$, PO(OR)(NRR'), $PO(NRR')_2$, $P(OR)_2$, P(OR)(NRR'), $P(NRR')_2$, SiRR'R'', $B(OR)_2$, C(O)R, NRR', $NO_2$, and halogen, each R, R' and R'' is independently selected from the group consisting of, H, $C_{1-4}$alkyl, hydroxy and $C_{1-4}$alkoxy, and each X and Y are independently anions selected from halide, OH, $HSO_4$, $SO_4$, $BF_4$, $SbF_6$, carboxylate, carbonate, hydrogencarbonate, $NO_3$, sulfonate, hexafluorophosphate, phosphate, hydrogen phosphate and perchlorate, Within this embodiment, the invention encompasses the aforementioned process wherein in Formula A each $R^A$ and each $R^B$ are independently selected from the group consisting of:

(i) hydrogen, (ii) halogen, (iii) $OR^7$, (iv) $N(R^7)_2$, (v) CN, (vi) $C_{1-8}$alkyl or $C_{2-8}$alkenyl, either of which optionally bears up to 3 substituents independently selected from halogen, OH, CN, $CF_3$, $OR^7$, $SR^8$, $SO_2R^8$, $SO_2N(R^7)_2$, $COR^7$, $CO_2R^7$, $CON(R^7)_2$, $N(R^7)_2$, $NR^7COR^8$ and $NR^7SO_2R^8$; and (vii) $C_{3-10}$cycloalkyl, $C_{3-10}$cycloalkyl$C_{1-4}$alkyl, Het, Het$C_{1-4}$alkyl, ARY or ARY-$C_{1-4}$alkyl, any of which optionally bears up to 3 substituents independently selected from halogen, OH, oxo, CN, $CF_3$, $R^8$, $OR^7$, $SR^8$, $SO_2R^8$, $SO_2N(R^7)_2$, $COR^7$, $CO_2R^7$, $CON(R^7)_2$, $N(R^7)_2$, $NR^7COR^8$ and $NR^7SO_2R^8$; where "ARY" refers to phenyl or 5- or 6-membered heteroaryl, either of which phenyl or heteroaryl is optionally fused to a 5- or 6-membered carbocycle or heterocycle, and "Het" refers to a nonaromatic mono- or bicyclic heterocyclic system of up to 10 ring atoms;

and one of $R^A$ and $R^B$ together may complete a mono- or bicyclic carbocyclic or heterocyclic system of up to 10 ring atoms which optionally bears up to 3 substituents independently selected from halogen, OH, oxo, CN, $CF_3$, $R^8$, $OR^7$, $SR^8$, $SO_2R^8$, $SO_2N(R^7)_2$, $COR^7$, $CO_2R^7$, $CON(R^7)_2$, $N(R^7)_2$, $NR^7COR^8$ and $NR^7SO_2R^8$;

$R^7$ is H or $C_{1-6}$alkyl which is optionally substituted with up to 3 halogen atoms or with OH, CN, $CF_3$, $C_{1-4}$alkoxy, amino, $C_{1-4}$alkylamino or di($C_{1-4}$alkyl)amino, or $R^7$ is phenyl, benzyl or 5- or 6-membered heteroaryl, any of which optionally bears up to 3 substituents independently selected from halogen, OH, CN, $CF_3$, $C_{1-4}$alkyl, $C_{1-4}$alkoxy, amino, $C_{1-4}$alkylamino and di($C_{1-4}$alkyl)amino;

or two $R^7$ groups attached to the same nitrogen atom may complete a heterocycle of up to 6 ring atoms which optionally bears up to 3 substituents independently selected from halogen, OH, oxo, CN, $CF_3$, $C_{1-4}$alkyl, $C_{1-4}$alkoxy, amino, $C_{1-4}$alkylamino and di($C_{1-4}$alkyl)amino; and $R^8$ is $C_{1-6}$alkyl which is optionally substituted with up to 3 halogen atoms or with OH, CN, $CF_3$, $C_{1-4}$alkoxy, amino, $C_{1-4}$alkylamino or di($C_{1-4}$alkyl)amino, or $R^8$ is phenyl, benzyl or 5- or 6-membered heteroaryl, any of which optionally bears up to 3 substituents independently selected from halogen, OH, CN, $CF_3$, $C_{1-4}$alkyl, $C_{1-4}$alkoxy, amino, $C_{1-4}$alkylamino and di($C_{1-4}$alkyl)amino;

or two $R^8$ groups attached to the same nitrogen atom may complete a heterocycle of up to 6 ring atoms which optionally bears up to 3 substituents independently selected from halogen, OH, oxo, CN, $CF_3$, $C_{1-4}$alkyl, $C_{1-4}$alkoxy, amino, $C_{1-4}$alkylamino and di($C_{1-4}$alkyl)amino.

Also within this embodiment, the invention encompasses the aforementioned process wherein in Formula A $R^C$ is selected from the group consisting of:

(i) hydrogen, (ii) halogen, (iii) $OR^7$, (iv) $N(R^7)_2$, (v) CN, (vi) $C_{1-8}$alkyl or $C_{2-8}$alkenyl, either of which optionally bears up to 3 substituents independently selected from halogen, OH, CN, $CF_3$, $OR^7$, $SR^8$, $SO_2R^8$, $SO_2N(R^7)_2$, $COR^7$, $CO_2R^7$, $CON(R^7)_2$, $N(R^7)_2$, $NR^7COR^8$ and $NR^7SO_2R^8$; and (vii) $C_{3-10}$cycloalkyl, $C_{3-10}$cycloalkyl$C_{1-4}$alkyl, Het, Het$C_{1-4}$alkyl, ARY or ARY-$C_{1-4}$alkyl, any of which optionally bears up to 3 substituents independently selected from halogen, OH, oxo, CN, $CF_3$, $R^8$, $OR^7$, $SR^8$, $SO_2R^8$, $SO_2N(R^7)_2$, $COR^7$, $CO_2R^7$, $CON(R^7)_2$, $N(R^7)_2$, $NR^7COR^8$ and $NR^7SO_2R^8$; where "ARY" refers to phenyl or 5- or 6-membered heteroaryl, either of which phenyl or heteroaryl is optionally fused to a 5- or 6-membered carbocycle or heterocycle, and "Het" refers to a nonaromatic mono- or bicyclic heterocyclic system of up to 10 ring atoms;

$R^7$ is H or $C_{1-6}$alkyl which is optionally substituted with up to 3 halogen atoms or with OH, CN, $CF_3$, $C_{1-4}$alkoxy, amino, $C_{1-4}$alkylamino or di($C_{1-4}$alkyl)amino, or $R^7$ is phenyl, benzyl or 5- or 6-membered heteroaryl, any of which optionally bears up to 3 substituents independently selected from halogen, OH, CN, $CF_3$, $C_{1-4}$alkyl, $C_{1-4}$alkoxy, amino, $C_{1-4}$alkylamino and di($C_{1-4}$alkyl)amino;

or two $R^7$ groups attached to the same nitrogen atom may complete a heterocycle of up to 6 ring atoms which optionally bears up to 3 substituents independently selected from halogen, OH, oxo, CN, $CF_3$, $C_{1-4}$alkyl, $C_{1-4}$alkoxy, amino, $C_{1-4}$alkylamino and di($C_{1-4}$alkyl)amino; and $R^8$ is $C_{1-6}$alkyl which is optionally substituted with up to 3 halogen atoms or with OH, CN, $CF_3$, $C_{1-4}$alkoxy, amino, $C_{1-4}$alkylamino or di($C_{1-4}$alkyl)amino, or $R^8$ is phenyl, benzyl or 5- or 6-membered heteroaryl, any of which optionally bears up to 3 substituents independently selected from halogen, OH, CN, $CF_3$, $C_{1-4}$alkyl, $C_{1-4}$alkoxy, amino, $C_{1-4}$alkylamino and di($C_{1-4}$alkyl)amino;

or two $R^8$ groups attached to the same nitrogen atom may complete a heterocycle of up to 6 ring atoms which optionally bears up to 3 substituents independently selected from halogen, OH, oxo, CN, $CF_3$, $C_{1-4}$alkyl, $C_{1-4}$alkoxy, amino, $C_{1-4}$alkylamino and di($C_{1-4}$alkyl)amino.

Also within this embodiment, the invention encompasses the aforementioned process wherein in Formula A PG is selected from the group consisting of: $C_{1-6}$ alkyl, vinyl, C(O)—O-L, C(O)-L, aryl, hetroaryl, benzyl, benzhydryl, trityl and $C_{1-6}$alkoxymethyl, wherein aryl, heteroaryl, benzyhydryl and trityl optionally are substituted with 1 to 3 substituents independently selected from methoxy and nitro, $C_{1-6}$alkoxymethyl is optionally substituted with trimethylsilyl and L is $C_{1-6}$alkyl, aryl or benzyl.

Also within this embodiment, the invention encompasses the aforementioned process wherein in Formula A W is selected from the group consisting of: halogen and sulfonate.

Also within this embodiment, the invention encompasses the aforementioned process wherein the water-immiscible organic phase is selected from the group consisting of benzene, toluene, xylenes, chlorobenzene, ethyl ether, isopropyl ether, tetrahydrofuran, 2-methyl tetrahydrofuran, dioxane, methyl tert-butyl ether, cyclopentyl methyl ether, isopropyl acetate, ethyl acetate, hexanes, heptanes, cyclohexane, dichloromethane and dichloroethane.

Also within this embodiment, the invention encompasses the aforementioned process the base is selected from the group consisting of: sodium hydroxide, lithium hydroxide, potassium hydroxide, sodium carbonate, lithium carbonate, potassium carbonate, cesium hydroxide, cesium carbonate, sodium hydrogen carbonate, potassium hydrogen carbonate, lithium hydrogen carbonate, cesium hydrogen carbonate, lithium fluoride, sodium fluoride, potassium fluoride, cesium fluoride, lithium tert-butoxide, sodium tert-butoxide, potassium tert-butoxide, sodium phosphate, lithium phosphate and potassium phosphate.

Also within this embodiment, the invention encompasses the aforementioned process wherein the water-immiscible organic phase is toluene and the base is sodium hydroxide.

The invention also encompasses the bis-quarternary cinchona alkaloid salts of Formula I for use as a phase transfer catalyst in one of the following reactions:

(1) the asymmetric formation of a carbon-carbon bond at position b of a substrate having the following formula

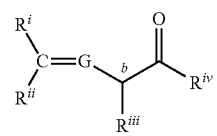

wherein:
G is N or CH,
$R^i$, $R^{ii}$ and $R^{iii}$ are independently H, halogen or an organic substituent group
$R^{iv}$ is selected from —$OR^v$, $SR^{vi}$ and $NR^{vii}R^{viii}$, wherein $R^v$ and $R^{vi}$ are independently 14 or an organic substituent group, $R^{vii}$ and $R^{viii}$ are independently H or an organic substituent group or $R^{vii}$ and $R^{viii}$ may be joined together with the nitrogen to which they are attached to form a 5- or 6-membered heterocyclic ring, and
when G is N, $R^{ii}$ and $R^{iii}$ may be joined together with the atoms to which they are attached to form a 5- or 6-membered mono- or 9- or 10-membered bi-cyclic ring containing one or more heteroatoms in addition to the nitrogen, said ring optionally substituted with 1 to 5 substituents independently selected from: halogen, hydroxy, amino or an organic substituent group;

(2) the asymmetric formation of a carbon-carbon bond at position b of a substrate having the following formula

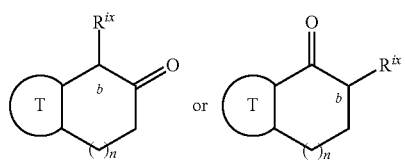

wherein n is 0 or 1, ring T is optional and forms a fused 5- or 6-membered aromatic carbocyclic or heterocyclic ring, each ring optionally substituted with hydrogen, halogen, hydroxy, amino or an organic substituent group and $R^{ix}$ is H or an organic substituent group, (3) the asymmetric formation of a carbon-carbon bond at position b of a substrate having the following formula

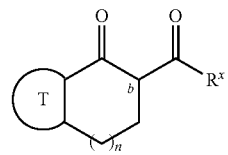

wherein n is 0 or 1, ring T is optional and forms a fused 5- or 6-membered aromatic carbocyclic or heterocyclic ring, each ring optionally substituted with hydrogen, halogen, hydroxy, amino or an organic substituent group and Rx is selected from —$OR^{xi}$, $SR^{xii}$ and $NR^{xiii}R^{xiv}$, wherein $R^{xi}$ and $R^{xii}$ are independently H or an organic substituent group and $R^{xiii}$ and $R^{xiv}$ are independently H or an organic substituent group or $R^{xiii}$ and $R^{xiv}$ may be joined together with the nitrogen to which they are attached to form a 5- or 6-membered heterocyclic ring;

(4) the asymmetric formation of a carbon-carbon bond position b of a substrate having the following formula

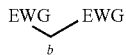

wherein each EWG is independently an electron withdrawing group;
comprising reacting the substrate with electrophilic alkylating agent, an electron deficient olefin or an aldehyde in the presence of bis-quarternary cinchona alkaloid salt and a base in a biphasic medium comprising an aqueous phase and organic phase to form the carbon-carbon bond.

The invention also encompasses bis-quarternary cinchona alkaloid salts having the chemical structure of Formula II:

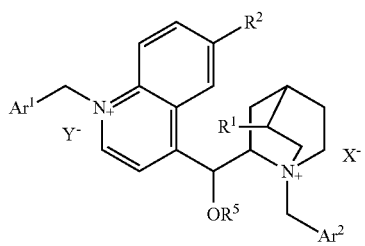

II wherein:
$R^1$ is selected from ethyl and vinyl,
$R^2$ is selected from hydrogen and methoxy,
$Ar^1$ is aryl or heteroaryl, wherein said aryl and heteroaryl groups are optionally substituted with one to five substituents independently selected from $R^3$,
$Ar^2$ is aryl or heteroaryl, wherein said aryl and heteroaryl groups are optionally substituted with one to five substituents independently selected from $R^3$,
each $R^3$ is independently selected from the group consisting of $C_{1-4}$ alkyl, $C_{1-4}$haloalkyl, aryl, $C_{1-4}$alkoxy, hydroxy, CN, $C_{1-4}$acyl, $N(R^4)_2$, $NO_2$, halogen, O-Phenyl and (C=O)$OC_{1-4}$alkyl,
each $R^4$ is independently H or $C_{1-4}$alkyl, and
each X and Y are independently anions selected from halide, OH, $HSO_4$, $SO_4$, $BF_4$, $SbF_6$, carboxylate, carbonate, hydrogencarbonate, $NO_3$, sulfonate, hexafluorophosphate, phosphate, hydrogen phosphate and perchlorate.

Unless depicted or specified otherwise, the cinchona alkaloid salts of Formula II encompass all stereoisomers, including cinchonine, cinchonidine, quinine, quinidine, dihydroquinidine, and dihydroquinine.

An embodiment of the invention encompasses bis-quarternary cinchona alkaloid salts of Formula II wherein $Ar^1$ is phenyl which is optionally substituted with one to five substituents independently selected from $R^3$, and $Ar^2$ is phenyl which is optionally substituted with one to five substituents independently selected from $R^3$.

An embodiment of the invention encompasses bis-quarternary cinchona alkaloid salts of Formula IIa

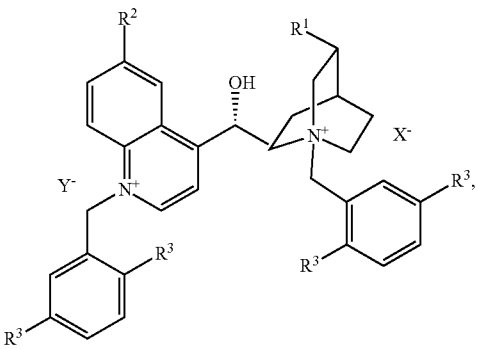

(IIa)

and otherwise as defined above.

An embodiment of the invention encompasses bis-quarternary cinchona alkaloid salts of Formula IIa wherein $R^1$ is vinyl and $R^2$ is methoxy.

Another embodiment of the invention encompasses bis-quarternary cinchona alkaloid salts of Formula IIa wherein $R^3$ is selected from halogen and methoxy.

Another embodiment of the invention encompasses a bis-quarternary cinchona alkaloid salt selected from:

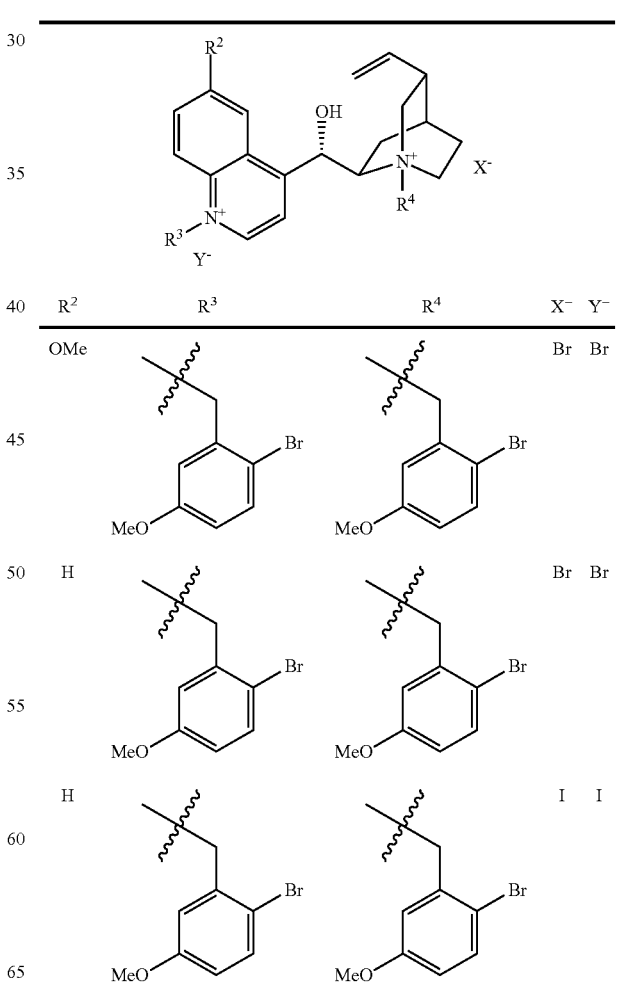

-continued
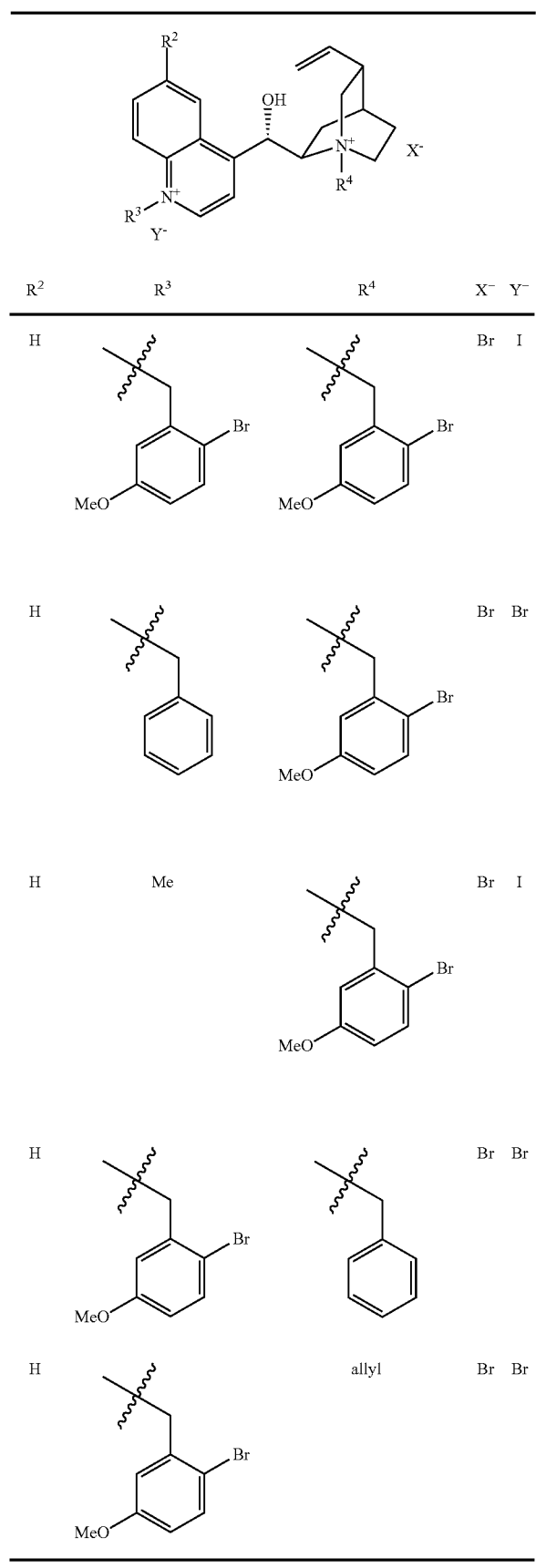
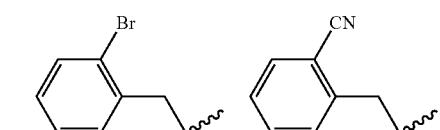
wherein R is selected from the group consisting of vinyl and ethyl;
$R^3$ is selected from the following groups:
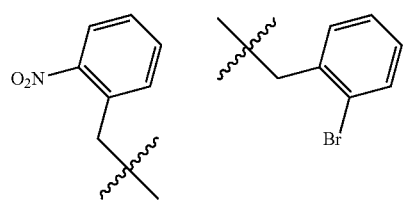
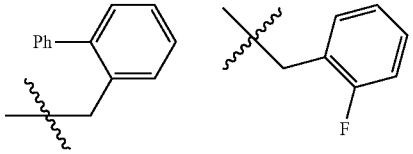
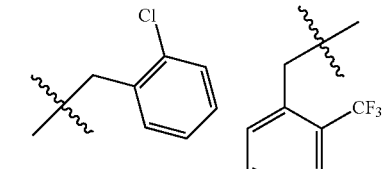
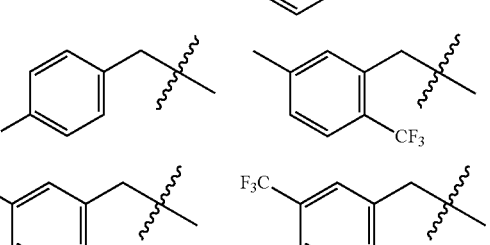
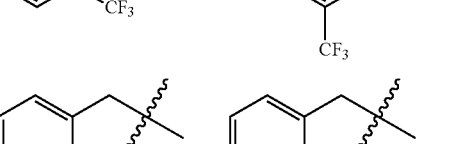
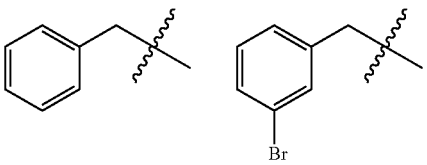

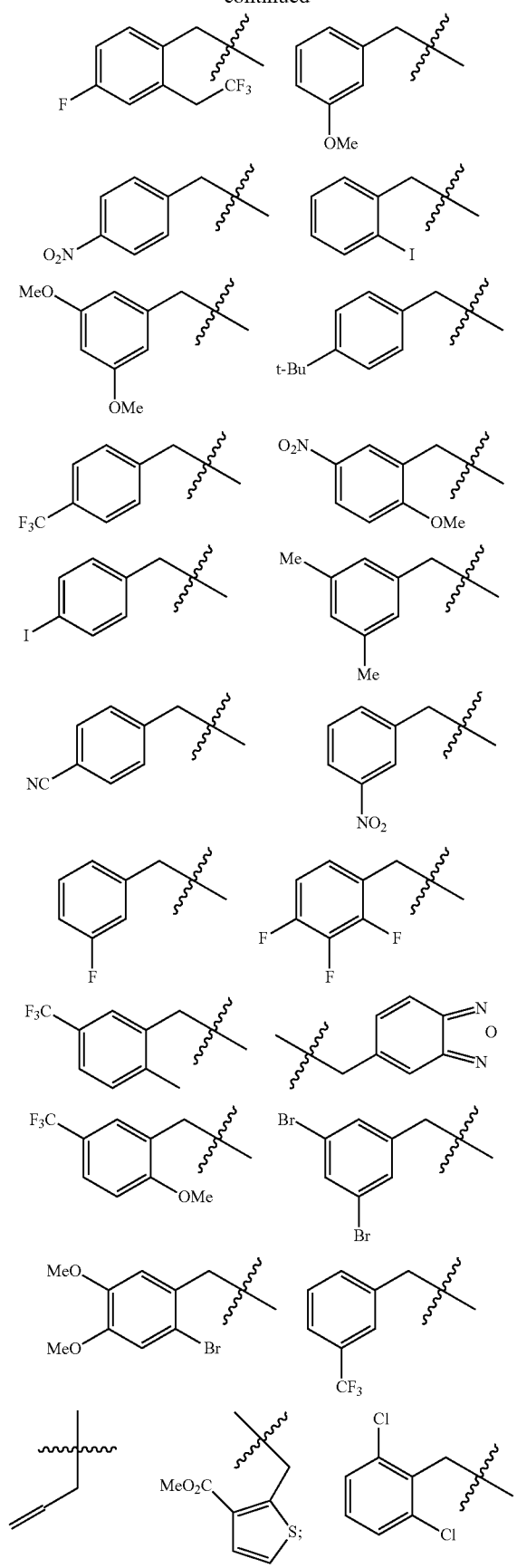
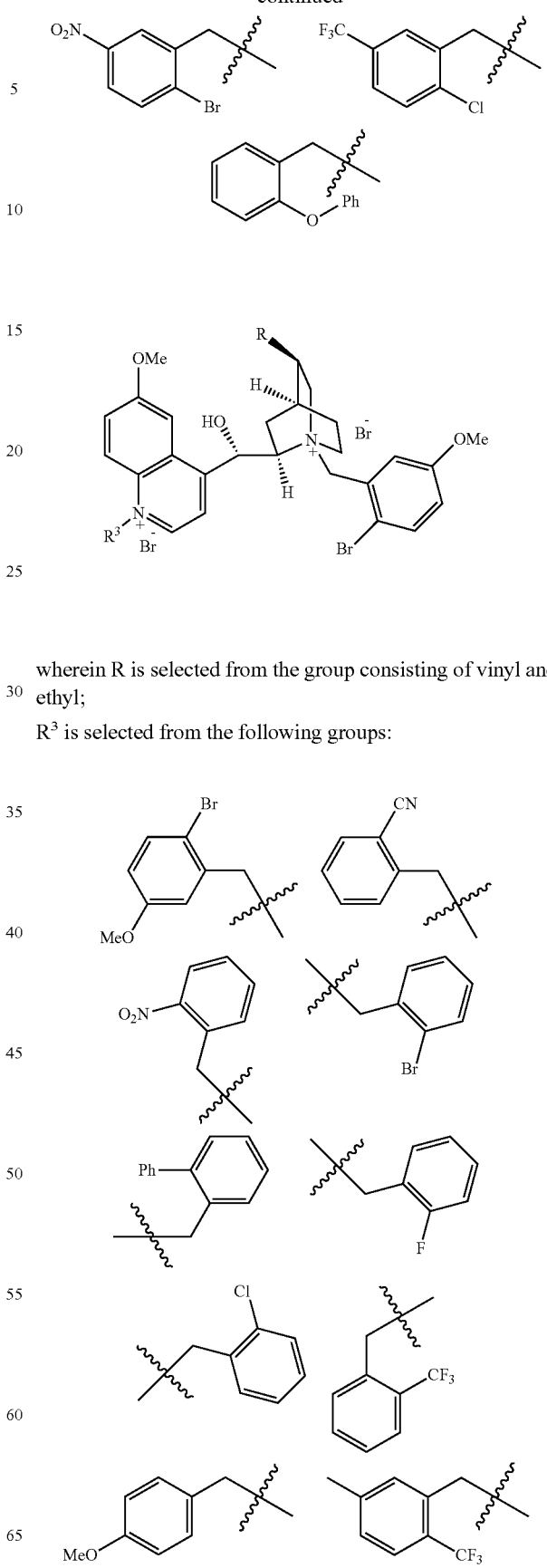
wherein R is selected from the group consisting of vinyl and ethyl;
R³ is selected from the following groups:

-continued
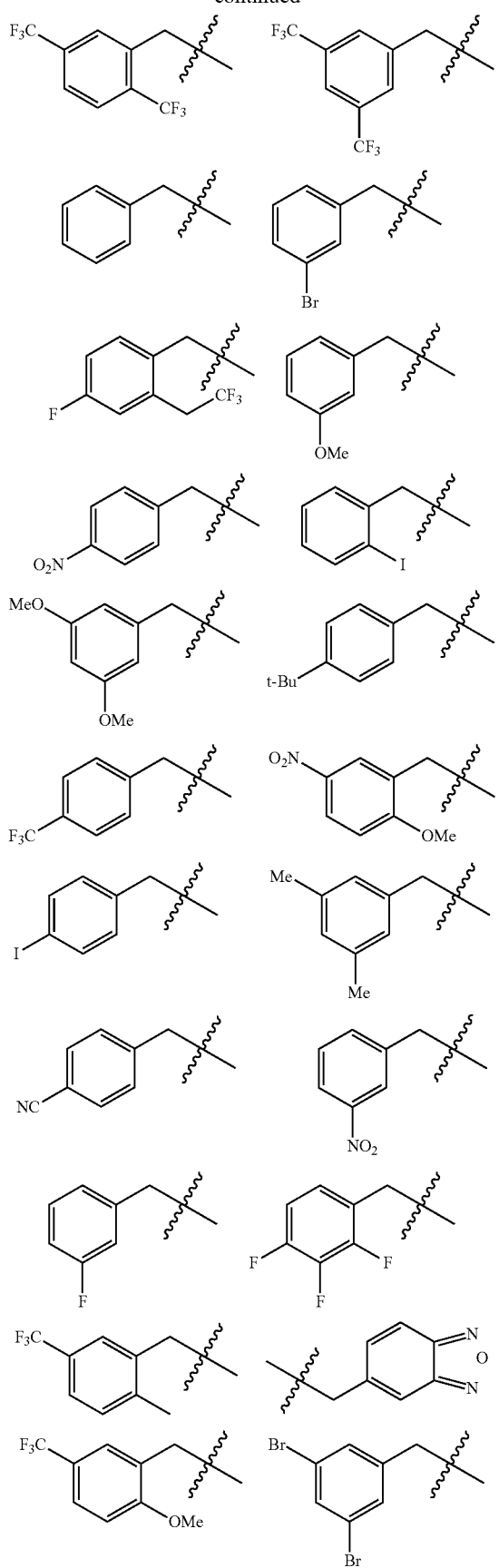
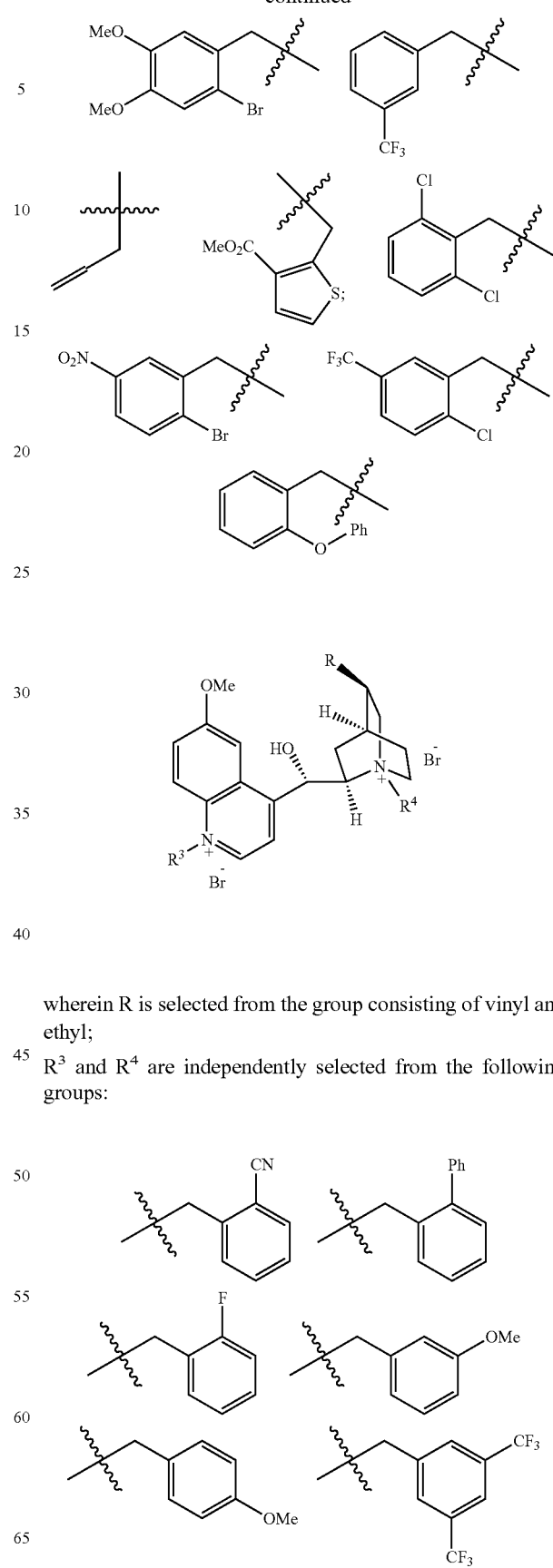
wherein R is selected from the group consisting of vinyl and ethyl;
$R^3$ and $R^4$ are independently selected from the following groups:
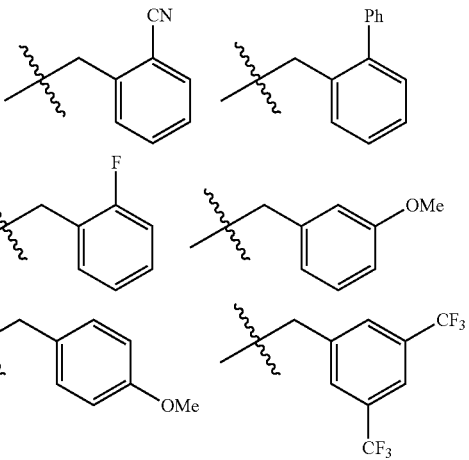

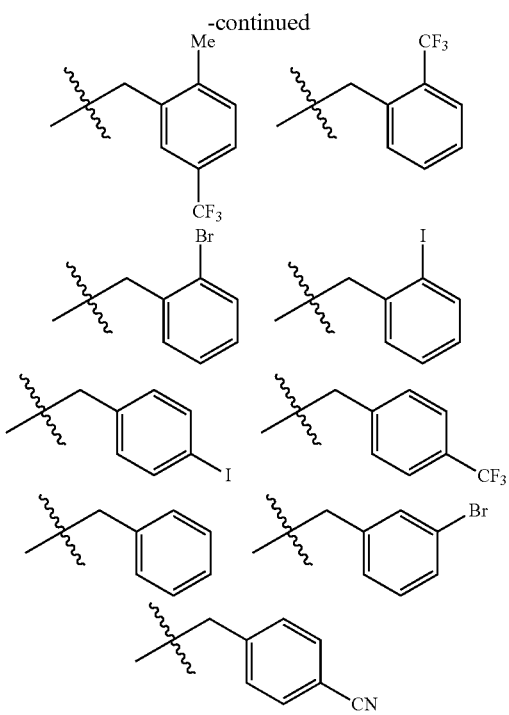

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and isopropyl, ethyl and methyl. As another example, "$C_{1-3}$ alkyl" refers to n-propyl, isopropyl, ethyl and methyl.

The term "haloalkyl" means an alkyl radical as defined above, unless otherwise specified, that is substituted with one to five, preferably one to three halogen. Representative examples include, but are not limited to trifluoromethyl, dichloroethyl, and the like.

The term acyl, means C(O)-alkyl where alkyl is as defined above.

The term "alkoxy" means —O-alkyl where alkyl is as defined above.

The term "alkenyl" refers to a monovalent straight or branched chain, saturated aliphatic hydrocarbon radical having a number of carbon atoms in the specified range and at least one carbon-carbon double bond, and otherwise carbon-carbon single bonds. Alkenyl includes for example ethenyl, 1-methylethynyl, 2-propenenyl, 2-butenyl, 1,4-pentadienyl and the like.

The term "alkynyl" refers to a monovalent straight or branched chain, saturated aliphatic hydrocarbon radical having a number of carbon atoms in the specified range and at least one carbon-carbon triple bond, and otherwise carbon-carbon double or single bonds. Alkynyl includes for example 2-propynyl, 1-butynyl, 3-hexen-5-ynyl and the like.

The term "cycloalkyl" refers to any monocyclic ring of an alkane having a number of carbon atoms in the specified range. Thus, for example, "$C_{3-6}$ cycloalkyl" (or "$C_3$-$C_6$ cycloalkyl") refers to cyclopropyl, cyclobutyl, cyclopentyl, and cyclohexyl, and "$C_{3-5}$ cycloalkyl" refers to cyclopropyl, cyclobutyl, and cyclopentyl.

The term "halogen" (or "halo") refers to fluorine, chlorine, bromine and iodine (alternatively referred to as fluoro, chloro, bromo, and iodo).

The term "aryl" refers to phenyl, naphthyl, and anthranyl.

The term "heteroaryl" refers to (i) a 5- or 6-membered heteroaromatic ring containing from 1 to 3 heteroatoms independently selected from N, O and S, or (ii) is a heterobicyclic ring selected from quinolinyl, isoquinolinyl, and quinoxalinyl. Suitable 5- and 6-membered heteroaromatic rings include, for example, pyridyl (also referred to as pyridinyl), pyrrolyl, pyrazinyl, pyrimidinyl, pyridazinyl, triazinyl, thienyl, furanyl, imidazolyl, pyrazolyl, triazolyl, oxazolyl, isooxazolyl, oxadiazolyl, oxatriazolyl, thiazolyl, isothiazolyl, and thiadiazolyl. Heteroaryls of particular interest are pyrrolyl, imidazolyl, pyridyl, pyrazinyl, quinolinyl (or quinolyl), isoquinolinyl (or isoquinolyl), and quinoxalinyl.

Examples of 4- to 7-membered, saturated heterocyclic rings within the scope of this invention include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated heterocyclic rings within the scope of this invention (see HetB) include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings listed above are not a limitation on the rings which can be used in the present invention. These rings are merely representative.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. As another example, an aryl or heteroaryl described as optionally substituted with "from 1 to 4 substituents" is intended to include as aspects thereof, an aryl or heteroaryl substituted with 1 to 4 substituents, 2 to 4 substituents, 3 to 4 substituents, 4 substituents, 1 to 3 substituents, 2 to 3 substituents, 3 substituents, 1 to 2 substituents, 2 substituents, and 1 substituent.

When any variable occurs more than one time in any constituent or in Formula I, II, IIa, A, B or C, or in any other formula depicting and describing compounds of the present invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., cycloalkyl, aryl, or heteroaryl) provided such ring substitution is chemically allowed and results in a stable compound.

The compounds of the invention contain chiral centers and, as a result of the selection of substituents and substituent patterns, can contain additional chiral centers, and thus can occur as mixtures of stereoisomers, or as individual diastereomers, or enantiomers. All isomeric forms of these compounds, whether individually or in mixtures, are within the scope of the present invention. Unless depicted or specified otherwise, the cinchona alkaloid salts of the invention encompass all stereoisomers, including cinchonine, cinchonidine, quinine, quinidine, dihydroquinidine, and dihydroquinine.

To the extent substituents and substituent patterns provide for the existence of tautomers (e.g., keto-enol tautomers) in the compounds of the invention, all tautomeric forms of these compounds, whether present individually or in mixtures, are within the scope of the present invention. Compounds of the present invention having a hydroxy substituent on a carbon atom of a heteroaromatic ring are understood to include compounds in which only the hydroxy is present, compounds in which only the tautomeric keto form (i.e., an oxo substitutent) is present, and compounds in which the keto and enol forms are both present.

The term "organic substituent group" means any substituent group containing a carbon atom, which may be optionally substituted. Organic substituent groups include, but are not limited to, $C_{1-10}$alkyl, $C_{2-10}$alkenyl, $C_{2-10}$alkynyl, aryl, heteroaryl, non- or partially aromatic heterocycles, $C_{3-10}$cycloalkyl, $C_{1-10}$alkoxy, $C_{1-10}$alkylthio, and $C_{1-10}$acyl, each optionally substituted with, for example, one or more of the following: halide, hydroxy, nitrogen containing substituents such as amino, sulfur containing substituent such as sulfates, $C_{1-4}$alkoxy and $C_{1-4}$alkylthio.

The term "nitrogen protecting group" means a substituent that protects a nitrogen atom in a reaction from a reagent or chemical environment. Nitrogen protecting groups are well known in the art and include for example, t-butyl, vinyl, phenyl, benzyl, p-methoxybenzyl, 3,4-dimethoxy benzyl, p-nitrobenzyl, benzhydryl, trityl, trialkylsilyl, methoxymethyl ether, (2,2,2-trichloroethoxy)methyl and 2-(trimethylsilyl)ethoxy)methyl, Boc, Cbz.

The term "functional group that has leaving ability" means an atom or atom group that leaves from a substrate in a substitution or elimination reaction, that is a leaving group, and includes for example halogen and sulfonate.

The term electrophilic alkylating agent" means an agent that delivers the equivalent of an alkyl cation, such as for example an alkyl halide.

The term "electron deficient olefin" means an electrophilic alkene substituted with for example, a ketone, such as an α,β-unsaturated carbonyl, a nitrile or a nitro group.

The term "sulfonate" means an anion or leaving group having the formula $R^{\#}$—$SO_3$— which is the conjugate base of sulfonic acid. $R^{\#}$ includes for example $C_{1-4}$alkyl optionally substituted with 1 to 3 halogen, and aryl optionally substituted with 1 to 3 halogen or methyl or nitro. Examples include mesylate, triflate, tosylate and besylate.

The term "electron withdrawing group" is well known in the art are includes for example, cyano, nitro, —C(O)OR$^{xvii}$, —C(O)SR$^{xviii}$ and —C(O)NR$^{xvix}$R$^{xx}$, wherein R$^{xvii}$ and R$^{xviii}$ are independently H or an organic substituent group and R$^{xvix}$ and R$^{xx}$ are independently H or an organic substituent group or R$^{xvix}$ and R$^{xx}$ may be joined together with the nitrogen to which they are attached to form a 5- or 6-membered heterocyclic ring;

ABBREVIATIONS

The following abbreviations are used throughout the specification.

DCM=dichloromethane
DCPP=1,3-bis(dicyclohexylphosphino)propane
DHP=3,4-dihydro-2H-pyran
DMF=dimethylformamide
DMSO=dimethyl sulfoxide
HCl=hydrochloric acid
IPA=isopropyl alcohol
LCAP=liquid chromatography area percent
MTBE=methyl tert-butyl ether
NMP=N-methyl-2-pyrrolidone
PTC=phase transfer catalyst
RT=room temperature
SFC=supercritical fluid chromatography
THF=tetrahydrofuran Example 1

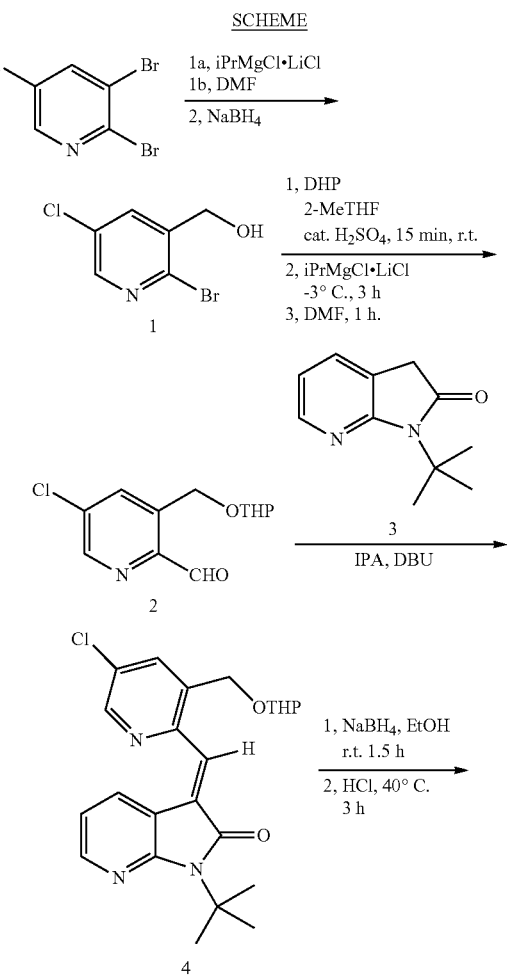

SCHEME

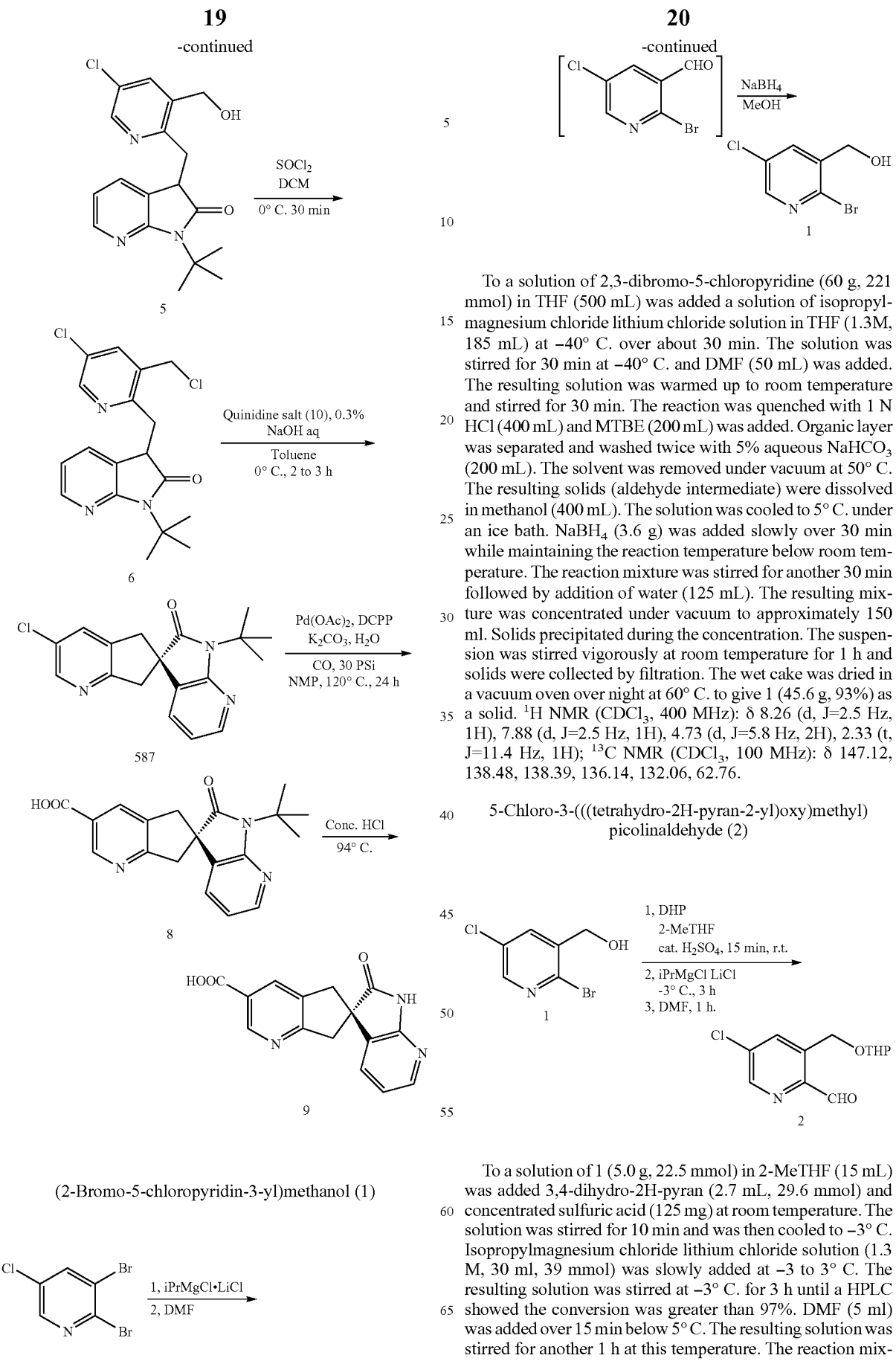

To a solution of 2,3-dibromo-5-chloropyridine (60 g, 221 mmol) in THF (500 mL) was added a solution of isopropylmagnesium chloride lithium chloride solution in THF (1.3M, 185 mL) at −40° C. over about 30 min. The solution was stirred for 30 min at −40° C. and DMF (50 mL) was added. The resulting solution was warmed up to room temperature and stirred for 30 min. The reaction was quenched with 1 N HCl (400 mL) and MTBE (200 mL) was added. Organic layer was separated and washed twice with 5% aqueous $NaHCO_3$ (200 mL). The solvent was removed under vacuum at 50° C. The resulting solids (aldehyde intermediate) were dissolved in methanol (400 mL). The solution was cooled to 5° C. under an ice bath. $NaBH_4$ (3.6 g) was added slowly over 30 min while maintaining the reaction temperature below room temperature. The reaction mixture was stirred for another 30 min followed by addition of water (125 mL). The resulting mixture was concentrated under vacuum to approximately 150 ml. Solids precipitated during the concentration. The suspension was stirred vigorously at room temperature for 1 h and solids were collected by filtration. The wet cake was dried in a vacuum oven over night at 60° C. to give 1 (45.6 g, 93%) as a solid. $^1$H NMR ($CDCl_3$, 400 MHz): δ 8.26 (d, J=2.5 Hz, 1H), 7.88 (d, J=2.5 Hz, 1H), 4.73 (d, J=5.8 Hz, 2H), 2.33 (t, J=11.4 Hz, 1H); $^{13}$C NMR ($CDCl_3$, 100 MHz): δ 147.12, 138.48, 138.39, 136.14, 132.06, 62.76.

5-Chloro-3-(((tetrahydro-2H-pyran-2-yl)oxy)methyl) picolinaldehyde (2)

To a solution of 1 (5.0 g, 22.5 mmol) in 2-MeTHF (15 mL) was added 3,4-dihydro-2H-pyran (2.7 mL, 29.6 mmol) and concentrated sulfuric acid (125 mg) at room temperature. The solution was stirred for 10 min and was then cooled to −3° C. Isopropylmagnesium chloride lithium chloride solution (1.3 M, 30 ml, 39 mmol) was slowly added at −3 to 3° C. The resulting solution was stirred at −3° C. for 3 h until a HPLC showed the conversion was greater than 97%. DMF (5 ml) was added over 15 min below 5° C. The resulting solution was stirred for another 1 h at this temperature. The reaction mixture was quenched by addition of MTBE (50 mL), 15% aqueous citric acid (25 mL) and water (15 mL). The organic layer was separated and washed with 5% aqueous NaCl (50 mL) twice. The organic solution was concentrated under vacuum at 50° C. to give 2 as an oil (6.2 g, 68 wt %, 16.6 mmol, 74% yield). The crude product was used directly for the next step without further purification. The pure sample was isolated by flash chromatography on silica gel with 5% ethyl acetate in hexane as eluants. $^1$H NMR (CDCl$_3$, 400 MHz): δ 10.13 (s, 1H), 8.65 (s, 1H), 8.20 (s, 1H), 5.25 (d, J=16.6 Hz, 1H), 5.01 (d, J=16.6 Hz, 1H), 4.80 (m, 1H), 3.88 (m, 1H), 3.58 (m, 1H), 1.7 (m, 6H); $^{13}$C NMR (CDCl$_3$, 100 MHz): δ 194.20, 147.06, 146.32, 138.98, 136.41, 134.87, 99.04, 64.42, 62.72, 30.53, 25.30, 19.66.

(E)-1-(tert-Butyl)-3-((5-chloro-3-(((tetrahydro-2H-pyran-2-yl)oxy)methyl)pyridin-2-yl)methylene)-1H-pyrrolo[2,3-b]pyridin-2(3H)-one (4)

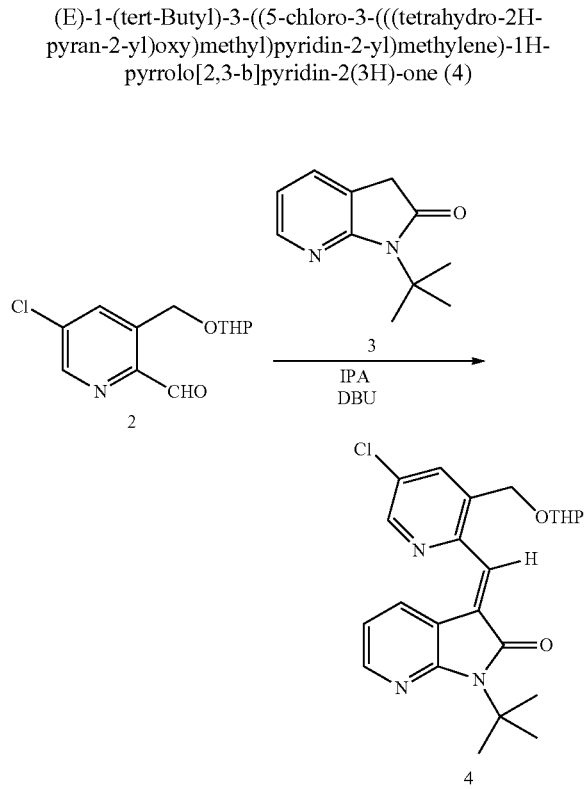

To a solution of crude 2 (6.2 g, 68 wt %, 16.6 mmol) and 3 (3.46 g, 18.3 mmol) in isopropanol (40 mL) was added DBU (0.12 g, 0.83 mmol) at −2° C. After stirring at −2° C. for 2 h, the solution was warmed up to 10° C. and stirred at this temperature for 3 h. The yellow solids precipitated from the solution. The suspension was stirred over night while the batch was allowed to warm up to room temperature slowly. The suspension was finally warm up to 50° C. and stirred for 4 h at this temperature. After cooling to 30° C., water (35 ml) was added dropwise over 30 min from an additional funnel. The suspension was cooled to room temperature and filtered. The cake was washed with a mixture of isopropanol (3 mL) and water (3 mL). The precipitates were collected and dried in a vacuum oven over night at 50° C. to give 4 (6.2 g, 87%) as a solid. $^1$H NMR (CDCl$_3$, 400 MHz): δ 8.72 (dd, J=7.5, 1.8 Hz), 8.66 (d, J=2.4 Hz, 1H), 8.18 (dd, J=5.1, 1.8 Hz, 1H), 7.94 (d, J=2.4 Hz, 1H), 7.78 (s, 1H, 1H), 6.89 (dd, J=7.5, 5.1 Hz, 1H), 4.99 (d, J=13.8 Hz, 1H), 4.80 (m, 1H), 4.70 (d, J=13.8 Hz, 1H), 3.90 (m, 1H), 3.60 (m, 1H), 1.83 (s, 9H), 2.0-1.5 (m, 6H). The conformation of the double bond as trans isomer was confirmed by NOE experiment. $^{13}$C NMR (CDCl$_3$, 100 MHz): δ 168.75, 159.64, 148.99, 147.85, 146.65, 137.01, 135.29, 133.56, 132.41, 129.50, 129.37, 117.27, 116.32, 98.77 64.80, 62.49, 58.62, 30.39, 29.01, 25.26, 19.34.

1-(tert-Butyl)-3-((5-chloro-3-(hydroxymethyl)pyridin-2-yl)methyl)-1H-pyrrolo[2,3-b]pyridin-2(3H)-one (5)

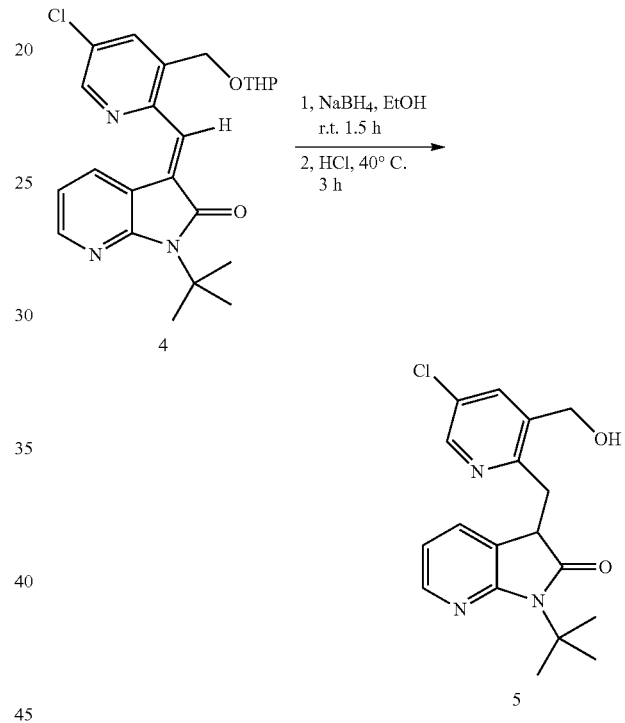

To a suspension of 4 (3.0 g, 7.0 mmol) in ethanol (25 mL) was added NaBH$_4$ (0.37 g) in one portion. The resulting suspension was stirred at room temperature for 1 h. The reaction was quenched by adding water (10 mL) followed by 6 N HCl solution in isopropanol (5 mL) slowly. The solution was warmed up to 40° C. and stirred for 3 h. The reaction mixture was mixed with MTBE (50 mL) and saturated aqueous NaCl (50 mL). The organic was separated and washed with water (50 mL). The solution was concentrated under vacuum at 50° C. and residue was triturated with hexane (30 mL). The resulting suspension was stirred at room temperature for 30 min. The precipitates were collected by filtration to give 5 (2.2 g, 86%) as a solid. $^1$H NMR (CDCl$_3$, 400 MHz): δ 8.34 (s, 1H), 8.15 (d, J=4.9 Hz, 1H), 7.74 (s, 1H), 7.30 (d, J=7.1 Hz, 1H), 6.83 (t, J=5.7 Hz, 1H), 4.73 (dd, J=13.4, 4.9 Hz, 1H), 4.63 (dd, J=13.4, 5.7 Hz, 1H), 4.01 (t, J=6.1 Hz, 1H), 3.44 (dd, J=15.4, 5.2 Hz, 1H), 3.17 (dd, J=15.4, 7.2 Hz, 1H), 2.94 (t, J=5.5 Hz, 1H), 1.79 (s, 9H); $^{13}$C NMR (CDCl$_3$, 100 MHz): δ 118.72, 159.12, 153.82, 146.45, 145.83 135.72, 135.32, 130.63, 130.27, 124.04, 117.33, 61.40, 58.70, 44.12, 34.01, 28.81.

1-(tert-Butyl)-3-((5-chloro-3-(chloromethyl)pyridin-2-yl)methyl)-1H-pyrrolo[2,3-b]pyridin-2(3H)-one (6)

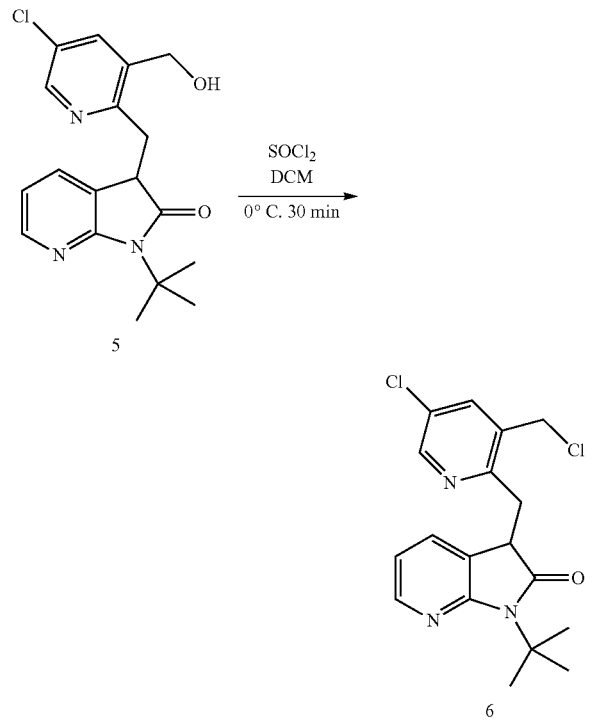 [SMILES: CC(C)(C)N1C(=O)C(Cc2ncc(Cl)cc2CO)c2cccnc21 ; CC(C)(C)N1C(=O)C(Cc2ncc(Cl)cc2CCl)c2cccnc21]

To a solution of 5 (5.8 g, 16.8 mmol) in dichloromethane (30 mL) was added DMF (60 μL) and thionyl chloride (2.2 g) at 5° C. The mixture was stirred for 30 min at this temperature followed by addition of 5% aqueous NaCl (30 mL). The organic layer was separated and washed with 5% aqueous NaCl (30 mL). The solvent was removed and the residue was dissolved in heptane (20 mL). The solution was stirred for 10 min and the product was precipitated. The suspension was cooled to 0° C. and filtered to give 6 (5.8 g, 93%) as a solid: $^1$H NMR (CDCl$_3$, 400 MHz): δ 8.36 (d, J=2.3 Hz, 1H), 8.13 (dd, J=5.1, 1.4 Hz, 1H), 7.65 (d, J=2.3 Hz, 1H), 7.19 (om, 1H), 6.78 (dd, J=7.3, 5.2 Hz, 1H), 4.58 (m, 2H), 4.06 (m, 1H), 3.66 (dd, J=16.3, 4.6 Hz, 1H), 3.32 (dd, J=16.3, 7.5 Hz, 1H), 1.75 (s, 9H); $^{13}$C NMR (CDCl$_3$, 100 MHz): δ 178.06, 159.45, 154.58, 147.39, 145.73, 136.87, 132.47, 130.42, 130.11, 123.77, 117.03, 58.51, 43.37, 42.25, 33.69, 28.82.

(S)-1'-(tert-Butyl)-3-chloro-5,7-dihydrospiro[cyclopenta[b]pyridine-6,3'-pyrrolo[2,3-b]pyridin]-2'(1'H)-one (7)

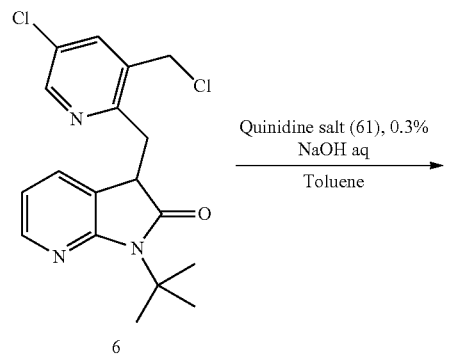

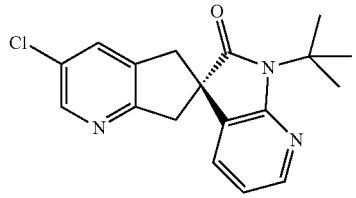

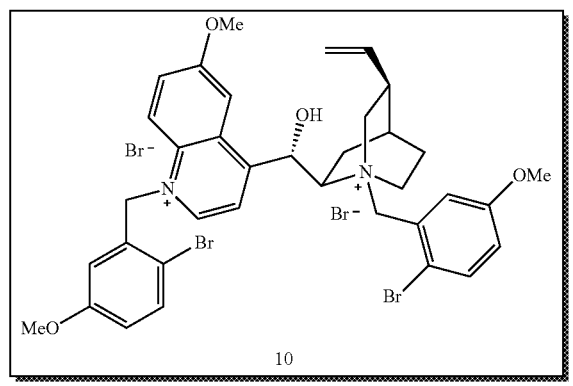

A solution of 6 (2.39 g, 6.56 mmol) in toluene (50 mL) was cooled to −2.5° C. under nitrogen atmosphere. Compound 10 (17 mg, 0.020 mmol) was charged, and the resulting solution was aged for about 15 min while cooled to −3.3° C. A pre-cooled (−1° C.) aqueous NaOH (26.2 mL, 0.3 N) was charged in over 4 min below −0.6° C. The reaction was aged at −1.3° C. for 3 h. The reaction was quenched with water (10 ml). The organic layer was washed with water (10 mL), concentrated, flushed with IPA to give crude product 7 (2.59 g, 94.4% ee, 83% wt by NMR against 1,3,5-trimethoxybenzene as an internal standard).

The crude product was recrystallized from IPA and water, filtered and dried in an oven at 50° C. to give 58 (1.95 g, 95.7% wt, 99% ee, 87% yield) as a solid. $^1$H NMR (CDCl$_3$, 400 MHz): δ 8.42 (s, 1H), 8.19 (d, J=5.2 Hz, 1H), 7.56 (s, 1H), 7.10 (d, J=7.3 Hz, 1H), 6.83 (dd, J=7.3, 5.2 Hz, 1H), 3.60 (dd, J=24.9, 16.8 Hz, 2H), 3.09 (dd, J=28.6, 16.8 Hz, 2H); $^{13}$C NMR (CDCl$_3$, 100 Hz): δ 179.43, 160.54, 157.82, 147.44, 146.54; 135.80, 132.17, 130.62, 129.33, 128.36, 117.69, 58.83, 51.94, 44.35, 41.57, 28.83.

(1S,2R,4S,5R)-1-(2-Bromo-5-methoxybenzyl)-2-((S)-(1-(2-bromo-5-methoxybenzyl)-6-methoxyquinolin-1-ium-4-yl)(hydroxy)methyl)-5-vinylquinuclidin-1-ium bromide (10)

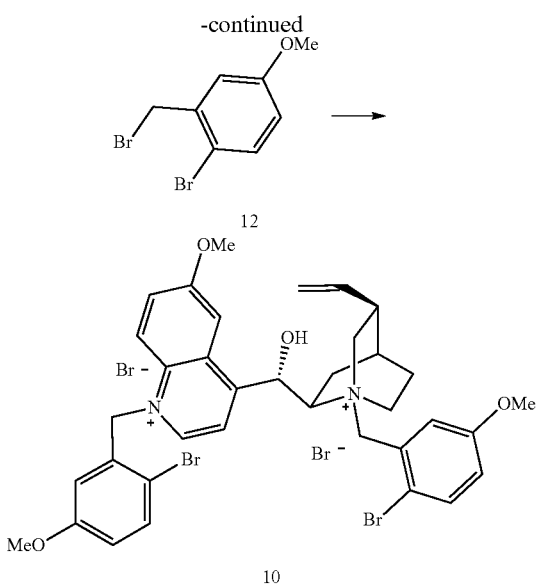

A slurry of quinidine (11, 8.1 g, 23.7 mmol, containing ~14% dihydroquinidine) and 2-bromo-5-methoxybenzylbromide (12, 16.59 g, 59.3 Mmol) in IPA (4.0 ml) and DMF (28.4 mL) was degassed by vacuum and flushed with N₂, then heated to 70° C. for 7 h. The reaction mixture was cooled to 22° C., this reaction solution was charged to AcOEt (320 ml) at 22° C. over 10 min while stirring. The resulting slurry was aged at 22° C. for 1 to 2 h, filtered, rinsed with AcOEt (2×24 ml), then hexane (2×24 ml). The solid was dried under vacuum to give powder as a mixture of bis-salts (bis-quinidine salt 10 and bis-dihydroquinidine salt). (Total 19.7 g, 94% yield). The authentic sample of 10 was purified by SFC (IC column, 20×250 mm, 60% MeOH/CO₂, 50 mL/min, 100 bar, 35° C., 220 nm, sample concentration: 133 mg/mL in MeOH; desired peak: 3 to 4.5 min). $^1$H NMR (CDCl₃, 500 MHz): δ 9.34 (d, J=6.1 Hz, 1H), 8.46 (d, J=6.1 Hz, 1H), 8.38 (d, J=9.7 Hz, 1H), 8.0 (dd, J=9.7, 2.1 Hz, 1H), 7.86 (s, 1H), 7.79 (d, J=8.9 Hz, 1H), 7.74 (d, J=8.9 Hz, 1H), 7.60 (d, J=2.5 Hz, 1H), 7.42 (d, J=2.3 Hz, 1H), 7.17 (dd, J=8.8, 2.8 Hz, 1H), 7.03 (dd, J=8.8, 2.7 Hz, 1H), 6.93 (s, 1H), 6.50 (d, J=2.4 Hz, 1H), 6.06 (m, 1H), 5.24 (m, 3H), 4.95 (d, J=12.9 Hz, 1H), 4.37 (m, 1H), 4.23 (m, 4H), 4.12 (m, 1H), 3.88 (s, 3H), 3.69 (s, 3H), 3.54 (m, 1H), 3.32 (s, 2H), 3.23 (m, 1H), 2.71 (m, 1H), 2.51 (s, 2H), 2.33 (m, 1H), 1.94 (br, 1H), 1.83 (br, 2H), 1.17 (br, 1H); $^{13}$C NMR (DMSO-d₆, 100 Hz): δ 159.45, 159.07, 158.67, 156.12, 146.01, 137.08, 134.68, 134.30, 133.21, 132.98, 128.18, 128.03, 127.45, 122.13, 121.89, 121.22, 118.08, 117.5, 117.07, 116.73, 116.20, 115.81, 112.67, 105.09, 66.81, 65.51, 62.43, 56.75, 56.06, 55.91, 55.52, 54.80, 36.84, 25.91, 23.10, 20.75.

(S)-1'-(tert-Butyl)-2'-oxo-1',2',5,7-tetrahydrospiro[cyclopenta[b]pyridine-6,3'-pyrrolo[2,3-b]pyridine]-3-carboxylic acid (8)

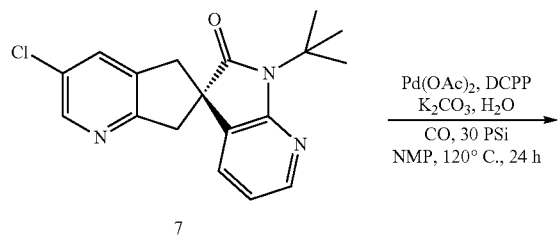

A mixture of 7 (5.0 g, 14.5 mmol), K₂CO₃ (5.01 g, 36.2 mmol), Pd(OAc)₂ (33 mg, 0.145 mmol), 1,3-bis(dicyclohexylphosphino)propane (DCPP, 127, mg, 0.290 mmol) and water (0.522 mL, 29.0 mmol) in NMP (32 mL) was heated at 120° C. under 30 psi of CO for 24 h. After cooling to room temperature, the resulted slurry was diluted with water (100 mL). The pH was slowly adjusted to 3~4 with 2 N HCl. The slurry was aged at room temperature for 1 h, filtered, rinsed with water (40 to 50 mL), dried under oven at 60° C. to give 8 (4.64 g, 95%) as a solid. $^1$H NMR (DMSO-d₆, 500 MHz): δ 8.90 (s, 1H), 8.19 (d, J=5.2 Hz, 1H), 7.54 (d, J=7.3 Hz, 1H,), 6.99 (dd, J=7.3, 5.2 Hz, 1H), 3.33 (m, 4H), 1.72 (s, 9H); $^{13}$C NMR (DMSO-d₆, 125 MHz): δ 180.16, 167.44, 166.97, 158.07, 149.76, 146.61, 135.39, 133.09, 130.36, 128.81, 125.48, 118.44, 58.19, 51.12, 44.56, 41.24, 28.91.

(S)-2'-Oxo-1',2',5,7-tetrahydrospiro[cyclopenta[b]pyridine-6,3'-pyrrolo[2,3-b]pyridine]-3-carboxylic acid (9)

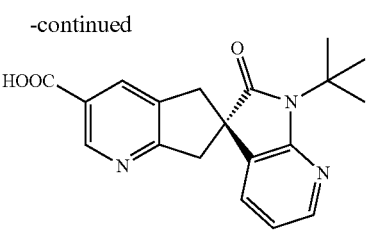

To 8 (4 g, 97% wt) was charged 37% HCl (40 to 44 mL). The slurry was heated at 94° C. for up to 48 h, cooled down to room temperature. The solvent was partially removed by reducing pressure to about total 2 vol (~4 mL water remained). The residue was diluted with water (20 mL) followed by adjusting pH to 2.6 with NaOH (3.5 N, 4.5 mL). The thick slurry was aged for 1 to 2 h, filtered, rinsed with water (2×8 mL), followed by water/acetone (1:1, 8 mL). The wet cake was dried to give compound 9 (3.1 g, 98% wt, 94%) as crystals. $^1$H NMR (DMSO-d₆, 500 MHz): δ 13.31 (br, 1H), 11.14 (s, 1H), 8.91 (s, 1H), 8.11 (m, 2H), 7.49 (dd, J=7.3, 1.3 Hz, 1H), 6.93 (dd, J=7.3, 5.3 Hz, 1H), 3.36 (m, 4H); $^{13}$C NMR (DMSO-d₆, 125 MHz): δ 181.06, 167.36, 166.95, 156.80, 149.79, 147.32, 135.37, 133.19, 130.73, 128.88, 125.50, 118.46, 51.78, 44.12, 40.70.

1-(tert-Butyl)-1H-pyrrolo[2,3-b]pyridin-2(3H)-one (3)

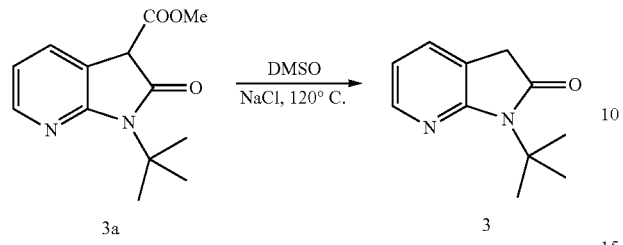

A mixture of compound 3a (10.0 g, 40.3 mmol), NaCl (2.9 g, 1.25 eq.) and water (2 mL) in DMSO (50 mL) was heated at 120° C. for 30 min. The mixture was cooled to 30° C. followed by addition of MTBE (200 mL) and water (50 mL). The organic layer was separated and the aqueous layer extracted with another MTBE (50 mL). Combined organic layer was washed three times with water (50 mL). Solvent removed under vacuum and the resulting solid was dried in a vacuum oven at 30° C. to give 3 (7.0 g, 92%) as solid. $^1$H NMR (CDCl$_3$, 400 MHz): δ 8.15 (dd, J=5.2, 1.4 Hz, 1H), 7.40 (dd, J=7.2, 1.4 Hz, 1H), 6.88 (dd, J=7.2, 5.2 Hz, 1H), 3.45 (s, 2H), 1.78 (s, 9H). $^{13}$C NMR (CDCl$_3$, 100 MHz): δ 174.99, 160.06, 145.82, 130.80, 119.51, 117.15, 58.53, 35.98, 28.80;

Example 2

SCHEME

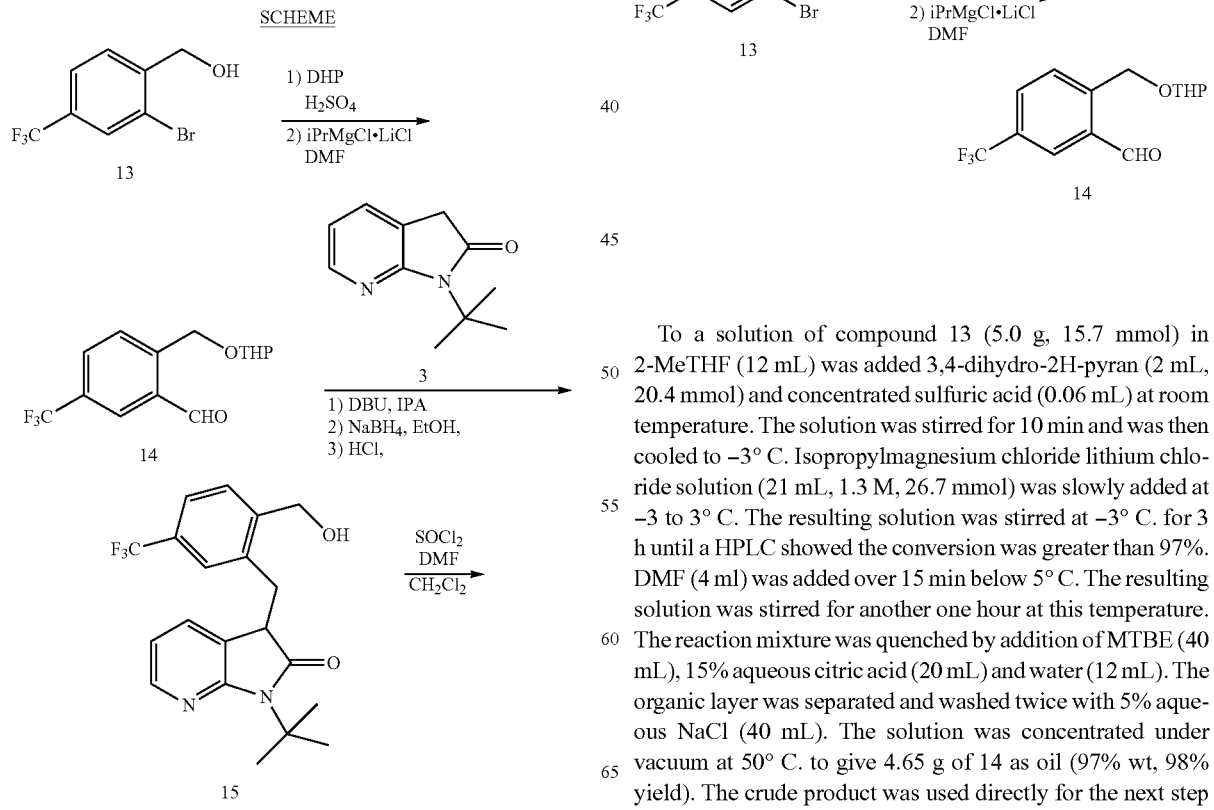

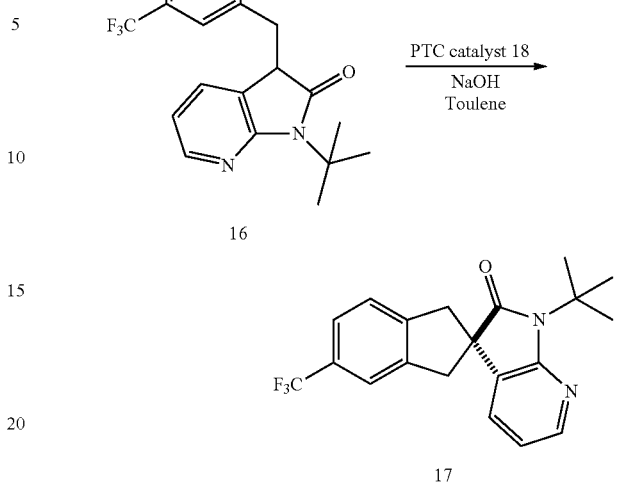

2-(((Tetrahydro-2H-pyran-2-yl)oxy)methyl)-5-(trifluoromethyl)benzaldehyde (14)

To a solution of compound 13 (5.0 g, 15.7 mmol) in 2-MeTHF (12 mL) was added 3,4-dihydro-2H-pyran (2 mL, 20.4 mmol) and concentrated sulfuric acid (0.06 mL) at room temperature. The solution was stirred for 10 min and was then cooled to −3° C. Isopropylmagnesium chloride lithium chloride solution (21 mL, 1.3 M, 26.7 mmol) was slowly added at −3 to 3° C. The resulting solution was stirred at −3° C. for 3 h until a HPLC showed the conversion was greater than 97%. DMF (4 ml) was added over 15 min below 5° C. The resulting solution was stirred for another one hour at this temperature. The reaction mixture was quenched by addition of MTBE (40 mL), 15% aqueous citric acid (20 mL) and water (12 mL). The organic layer was separated and washed twice with 5% aqueous NaCl (40 mL). The solution was concentrated under vacuum at 50° C. to give 4.65 g of 14 as oil (97% wt, 98% yield). The crude product was used directly for the next step without further purification.

1-(tert-Butyl)-3-(2-(hydroxymethyl)-5-(trifluoromethyl)benzyl)-1H-pyrrolo[2,3-b]pyridin-2(3H)-one (15)

1-(tert-Butyl)-3-(2-(chloromethyl)-5-(trifluoromethyl)benzyl)-1H-pyrrolo[2,3-b]pyridin-2(3H)-one (16)

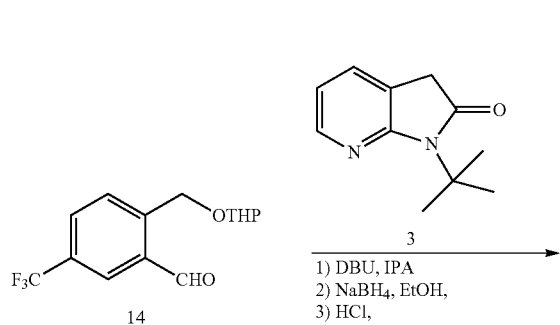

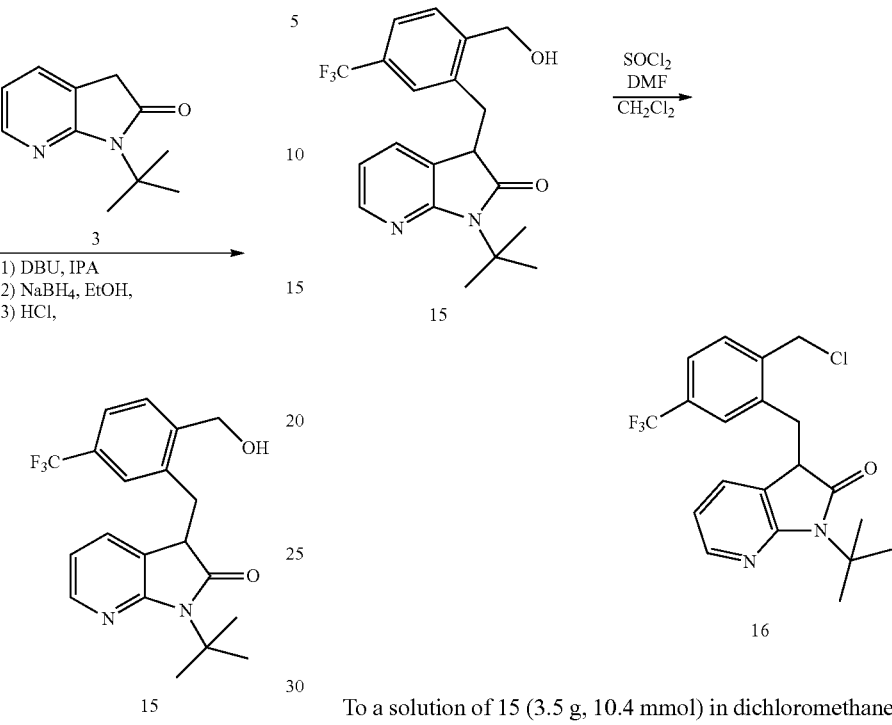

To a solution of 15 (3.5 g, 10.4 mmol) in dichloromethane (20 mL) was charged DMF (0.04 mL, 0.5 mmol). This solution was cooled under an ice bath. Thionyl chloride (0.85 mL, 11.5 mmol) was then added under 5° C., and the resulting reaction was aged for 3 h at this temperature. Once the reaction was complete, 5% aqueous NaCl (16.5 mL) was added. The organic layer was separated and washed with 5% aqueous NaCl (16.5 mL). The solvent was removed via rotovap, and the crude was purified by silica gel column chromatography (0 to 10% AcOEt/hexane) to give the desired compound 16 as an oil (3.05 g, 74%). $^1$H NMR (CDCl$_3$, 500 MHz): δ 8.20 (dd, J=5.1, 1.7 Hz, 1H), 7.58 (d, J=8.1 Hz, 1H), 7.51 (dd, J=8.1, 1.1 Hz, 1H), 7.18 (s, 1H), 7.12 (dd, J=6.3, 2.7 Hz, 1H), 6.88 (dd, J=7.3, 5.1 Hz, 1H), 4.77 (ABq, J=12.9 Hz, 2H), 3.72 (m, 1H), 3.46 (dd, J=14.2, 4.4, 1H), 3.18 (dd, J=14.2, 8.7 Hz, 1H), 1.67 (s, 9H); $^{13}$C NMR (CDCl$_3$, 125 MHz): δ 177.6, 159.1, 146.5, 143.3, 136.6, 131.0, 129.7 (m, 2C), 124.0, 123.0, 123.9 (q, J=271 Hz), 117.4, 126.6, 62.4, 58.8, 46.1, 32.9, 28.6.

To a round bottom flask was charged 14 (4.50 g, 15.6 mmol), 3 (2.50 g, 17.2 mmol, 1.1 eq.) and IPA (25 ml). This slurry was aged until dissolved. It was cooled under an ice bath followed by charging DBU (0.12 mL, 0.8 mmol) then was aged for half hour below 5° C. and 2 h at room temperature. The reaction mixture was degassed by vacuum and flushed with N$_2$ followed by charge NaBH$_4$ (0.80 g, 21.8 mmol). The reaction was aged for 2 h. After completion of the reduction, 6 N HCl (10 mL) and water (16 mL) was added in and the mixture was heated to 70° C. for 1 to 2 h until the deprotection of THP was complete. The resulting reaction mixture was concentrated followed by charge dichloromethane (60 mL) and water (27 mL). The pH of the reaction mixture was adjusted to ~10 with aqueous NaOH, and the organic layer was separated. The aqueous layer was then extracted with dichloromethane (50 mL) twice. The combined organic layer was concentrated under vacuum, and purified with silica gel column (0 to 30% of AcOEt/hexane) to give the desired product 15 as a solid (4.07 g, 78%).

$^1$H NMR (CDCl$_3$, 500 MHz): δ 8.21 (dd, J=5.2, 0.8 Hz, 1H), 7.59 (d, J=8.1 Hz, 1H), 7.52 (dd, J=8.0, 1.1 Hz, 1H), 7.19 (om, 2H), 6.90 (dd, J=7.3, 5.3 Hz, 1H), 4.78 (ABq, J=12.9 Hz, 2H), 3.71 (m, 1H), 3.45 (dd, J=14.2, 4.4 Hz, 1H), 3.22 (dd, J=14.2, 4.4 Hz, 1H), 2.77 (br, 1H), 1.67 (s, 9H); $^{13}$C NMR (CDCl$_3$, 125 MHz): δ 176.6, 159.1, 146.3, 140.1, 137.4, 131.13, 131.10, 130.7 (q, J=33.8 Hz), 127.3, 124.3, 123.5 (q, J=272 Hz), 122.5, 117.1, 58.7, 45.7, 43.0, 33.0, 28.7.

1'-(tert-Butyl)-5-(trifluoromethyl)-1,3-dihydrospiro[indene-2,3'-pyrrolo[2,3-b]pyridin]-2'(1'H)-one (17)

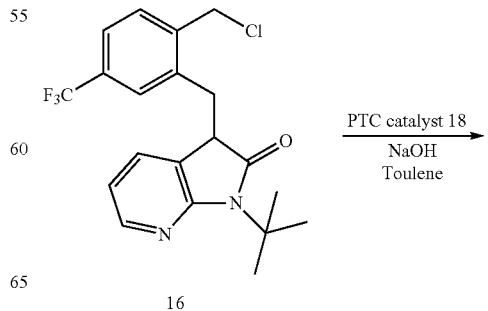

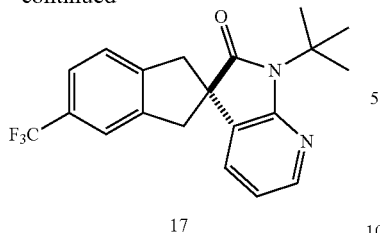

17

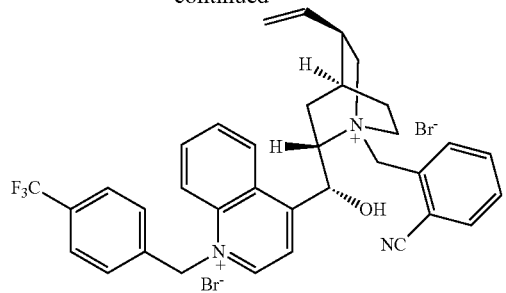

18

A solution of 16 (50 mg, 0.126 mmol) in toluene (2 ml) was cooled to −1° C., degassed with vacuum and flushed N₂. To this solution was charged a precooled (−2 to 0° C.) aqueous NaOH (1N, 1 mL) followed by charged a catalyst 18. The resulted reaction was aged at −1 to 1° C. for several hours until complete conversion. The organic layer was purified with silica gel column chromatography (0 to 10% AcOEt/hexane) to give the desired compound 17 as oil (42 mg, 92% IY, 85% ee, R or S undetermined).

¹H NMR (CDCl₃, 400 MHz): δ 8.17 (dd, J=5.2, 1.8 Hz, 1H), 7.52 (m, 2H), 7.37 (d, J=8.2 Hz, 1H), 7.02 (dd, J=7.3, 1.8 Hz, 1H), 6.80 (dd, J=7.3, 5.2 Hz, 1H), 3.64 (d, J=15.9 Hz, 2H), 3.09 (d, J=16.1 Hz, 2H), 1.83 (s, 9H); ¹³C NMR (CDCl₃, 125 MHz): δ 179.6, 157.6, 146.3, 145.3, 141.9, 129.8, 129.6 (q, J=32 Hz), 127.6, 124.8, 124.5 (q, J=271 Hz), 121.4, 117.6, 58.7, 53.8, 43.8, 43.7, 28.9.

(1S,2S,4S,5R)-1-(2-Cyanobenzyl)-2-((R)-hydroxy (quinolin-4-yl)methyl)-5-vinylquinuclidin-1-ium bromide (19) and (1S,2S,4S,5R)-1-(2-cyanobenzyl)-2-((R)-hydroxy(1-(4-(trifluoromethyl)benzyl)quinolin-1-ium-4-yl)methyl)-5-vinylquinuclidin-1-ium bromide (18)

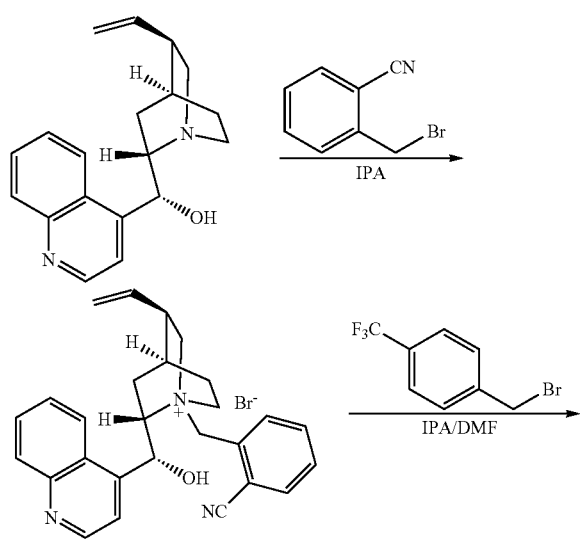

19

Preparation of 19

A slurry cinchonidine (5.0 g, 16.98 mmol) and 2-cyanobenzyl bromide (4.0 g, 20.38 mmol) in 50 ml of IPA was degassed by vacuum and flushed with N₂, then it was heated to 67° C. until completely conversion (4 to 5 h). It was cooled down and 40 mL of solvent was removed by reducing pressure. This concentrated solution was added into AcOEt (160 ml) over 5 to 10 min while stirring. The resulting slurry was aged for 1 to 2 h at 22° C., filtered, rinsed with IPA/hexane (1:1; 50 ml) and dried under vacuum to give 19 as a solid (7.43 g, 89% IY). ¹H NMR (DMSO-d₆, 500 MHz): δ 9.00 (d, J=4.5 Hz, 1H), 8.39 (d, J=8.4 Hz, 1H), 8.17 (d, J=7.6 Hz, 1H), 8.12 (d, J=7.6 Hz, 2H), 7.97 (t, J=7.8 Hz, 1H), 7.85 (m, 3H), 7.76 (t, J=8.2 Hz, 1H), 6.87 (d, J=3.0 Hz, 1H), 6.58 (s, 1H), 5.72 (m, 1H), 5.33 (q, J=13.1 Hz, 2H), 5.21 (d, J=17.3 Hz, 1H), 4.96 (d, J=10.6 Hz, 1H), 4.47 (br, 1H), 4.07 (t, J=9.8 Hz, 1H), 3.94 (dt, J=12.0, 3.6 Hz, 1H), 3.44 (t, J=12.0 Hz, 1H), 3.30 (dt, J=11.5, 4.1 Hz, 1H), 2.68 (br, 1H), 2.13 (m, 2H), 2.02 (s, 1H), 1.81 (m, 1H), 1.22 (m, 1H); ¹³C NMR (DMSO-d₆, 125 MHz): δ 150.1, 147.6, 145.0, 138.0, 135.7, 134.3, 133.6, 131.1, 130.8, 129.8, 129.4, 127.1, 124.2, 123.6, 120.0, 117.8, 116.4, 115.7, 67.7, 64.7, 60.4, 59.3, 51.2, 37.0, 25.5, 24.3, 21.1.

Preparation of 18

A slurry of 19 (0.15 g, 0.306 mmol) and 2-nitrobenzyl bromide (0.104 g, 0.61 mmol) in IPA (0.075 mL) and DMF (0.53 mL) was degassed by vacuum and flushed with N₂, then it was heated to 70° C. until completely conversion (4 to 5 h). It was cooled down and was added into AcOEt (6 ml) over 5 to 10 min. The resulting slurry was aged for 1 to 2 h at 22° C., filtered, rinsed AcOEt (2×5 ml) and dried under vacuum to give 18 as a solid (0.19 g, 94% IY). ¹H NMR (DMSO-d₆, 500 MHz): δ 9.82 (d, J=6.3 Hz, 1H), 8.81 (d, J=8.5 Hz, 1H), 8.55 (m, 1H), 8.30 (t, J=7.4 Hz, 1H), 8.13 (m, 3H), 8.0 (t, J=7.4 Hz, 1H), 7.82 (m, 3H), 7.63 (d, J=8.1 Hz, 2H), 7.45 (d, J=3.5 Hz, 1H), 6.86 (s, 1H), 6.50 (m, 2H), 6.5 (m, 2H), 5.70 (m, 1H), 5.33 (s, 2H), 5.21 (d, J=17.4 Hz, 1H), 4.99 (d, J=10.5 Hz, 1H), 4.49 (m, 1H), 4.15 (m, 1H) 3.90 (m, 1H), 3.53 (m, 1H), 3.38 (m, 1H), 2.70 (br, 1H), 2.10 (m, 3H), 1.88 (m, 1H), 1.48 (m, 1H); ¹³C NMR (DMSO-d₆, 125 MHz): δ 158.4, 149.8, 138.3, 138.0, 137.2, 135.8, 135.6, 134.3, 133.7, 131.2, 130.6, 130.5, 129.2 (q, J=32.0 Hz), 128.3 (2C), 126.7, 126.2, 125.99, 125.96, 123.9 (q, J=272.5 Hz), 122.8, 121.6, 119.8, 117.8, 116.7, 115.7, 67.3, 65.4, 60.4, 59.7, 59.4, 51.3, 37.0, 30.9, 25.5, 24.9, 22.0.

Results

As shown in Table 1, the bis-quaternary catalyst is much more active and efficient as compared to the mono-quaternary catalyst for the spirocyclization reaction shown. For this experiment, the bis-catalysts contained ~12 to 15% of the double saturated compounds hydroquinidine or hydrocinchonine.

TABLE 1

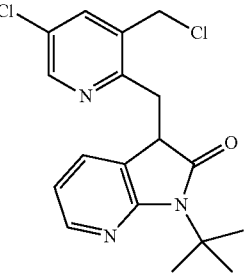

| PTC catalyst: | Loading | EE | conversion | Yield |
|---|---|---|---|---|
| 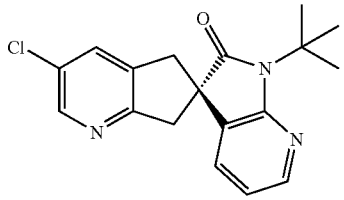 | 3% | 58% | 80% | ND |
| 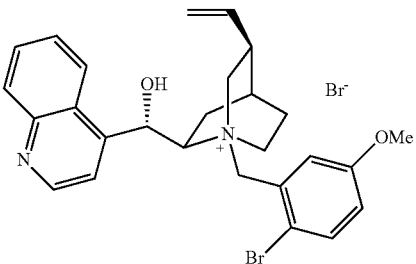 | 0.3% | 92% | 100% | 98% AY |
|  | 0.3% | 94.4% | 100% | 100% |

Tables 2 and 3 show a SAR study of bis-quaternary PTC catalysts for spirocyclization. Both bis-quaternary quinidine and cinchonine catalysts are very efficient (Entries 2 to 5). The Bis-Quinidine catalyst is relatively better than bis-cinchonine catalyst (Entry 2 and 3). 2-Bromo-5-Methoxy-benzyl group is the optimized group for this reaction.

TABLE 2
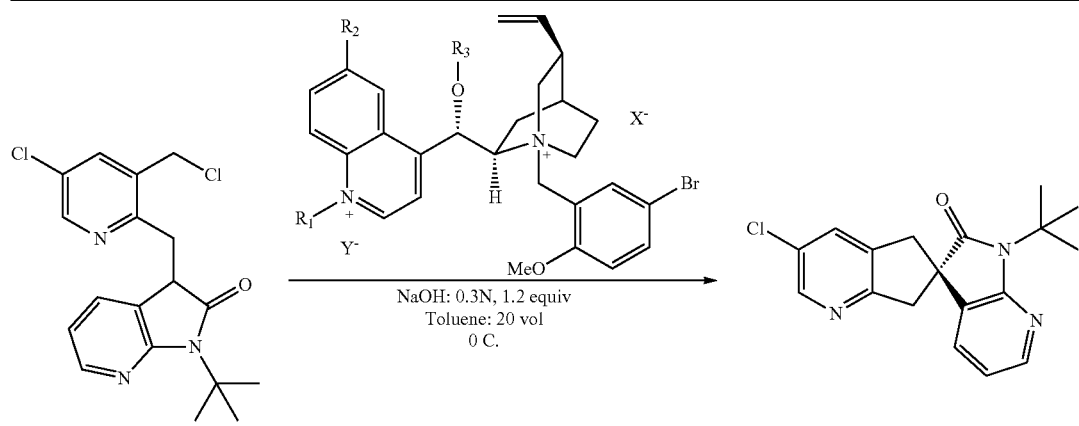
| Entry | R1 | R2 | R3 | X | Y | % ee |
|---|---|---|---|---|---|---|
| 1 | No-substitution | H | H | Br | None | 58% ee |
| 2 | ⌇⌇-C6H3(2-Br)(5-OMe) | OMe | H | Br | Br | 94.4% ee |
| 3 | ⌇⌇-C6H3(2-Br)(5-OMe) | H | H | Br | Br | 90% ee |
| 4 | ⌇⌇-C6H3(2-Br)(5-OMe) | H | H | I | I | 89.7% ee |
| 5 | ⌇⌇-C6H3(2-Br)(5-OMe) | H | H | Br | I | 89.4% ee |
| 6 | ⌇⌇-C6H5 | H | H | Br | Br | 84.8% ee |

TABLE 2-continued

| Entry | R1 | R2 | R3 | X | Y | % ee |
|---|---|---|---|---|---|---|
| 7 | Me | H | H | Br | I | 80% ee |
| 8 | No-substitution | H | 2-Br-5-MeO-benzyl | Br | None | 67% ee |
| 9 | 2-Br-5-MeO-benzyl | H | 2-Br-5-MeO-benzyl | Br | Br | 27% ee |

TABLE 3

| R4 | EE | Conversion |
|---|---|---|
| Benzyl | 66.3% ee | 93% |
| Allyl | 69.7% ee | 100% |
| 2-Br-5-MeO-benzyl | 92% ee | 100% |

Table 4 shows a study of different functional groups.

TABLE 4

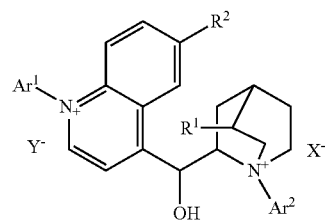

| Entry | X¹ | Y¹ | % ee |
|---|---|---|---|
| 1 | Cl | Cl | 92 |
| 2 | Br | Cl | 92 |
| 3 | CO₂Me | Cl | 92 |
| 4 | Br | Tos | 51 |
| 5 | Br | Br | 70 |

Table 5 shows a study of different ring systems; Doubly quaternized PTC is a more active catalyst than mono quaternized PTC.

TABLE 5

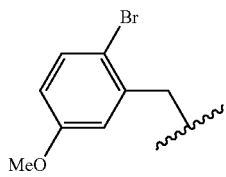 [SMILES: *Cc1cc(OC)ccc1Br]

16
PTC 19: 3% ee
PTC 18: 85% ee

17
Absolute configuration (R or S) has not been determined.

What is claimed is:

1. A bis-quaternary alkaloid salt having the chemical structure of Formula II:

II wherein:
R¹ is ethyl or vinyl;
R² is hydrogen or methoxy;
Ar¹ and Ar² are defined as follows:
I) Ar¹ is:

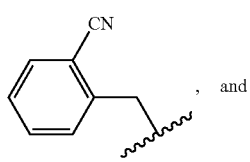 [SMILES: *Cc1ccccc1C#N]

and Ar² is allyl; or
(II) Ar² is:

, and

Ar¹ is:

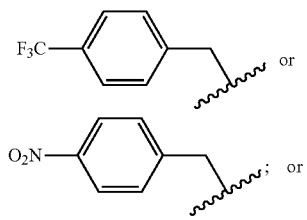

(II) Arᵉ is:

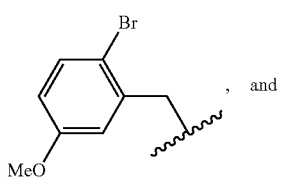 [SMILES: *Cc1cc(OC)ccc1Br], and

Ar¹ is:

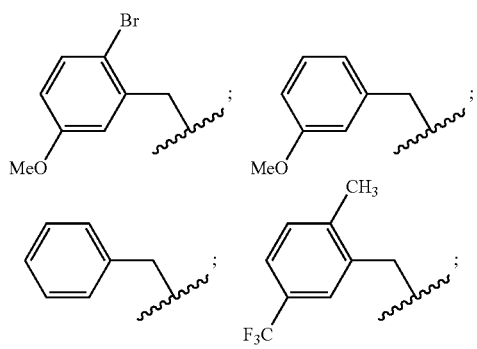

or —CH₃; and,
X and Y are independently a halide anion.

2. A bis-quaternary alkaloid salt of claim 1 having the structure of Formula IIa

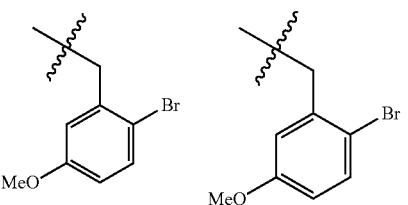 IIa wherein R¹ is vinyl or ethyl, R² is —H or MeO—, and X and Y are independently a halide.

3. The bis-quaternary cinchona alkaloid salt of claim 2 wherein R¹ is vinyl and R² is methoxy.

4. The bis-quaternary cinchona alkaloid salt of claim 3 wherein X and Y are independently Br or I.

5. A bis-quaternary alkaloid salt having the structure:

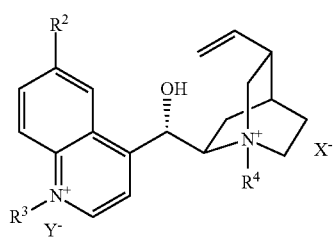 (I)

wherein:

| R² is | R³ is | R⁴ is | X⁻ is | Y⁻ is |
|---|---|---|---|---|
| OMe |  | | Br | Br; |
| H | 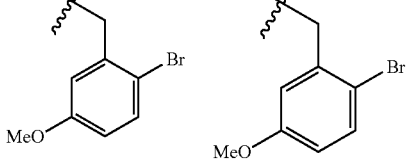 | | Br | Br; |
| H | 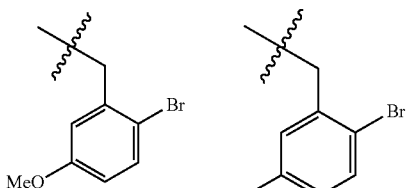 | | I | I; |
| H | 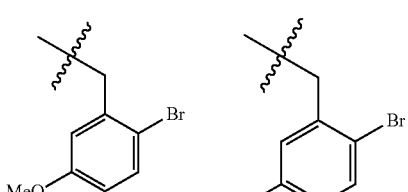 | | Br | I; |

| R² is | R³ is | R⁴ is | X⁻ is | Y⁻ is |
|---|---|---|---|---|
| H | 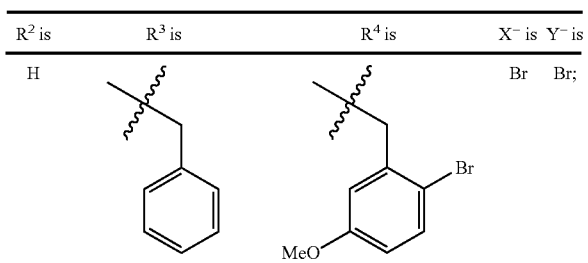 | 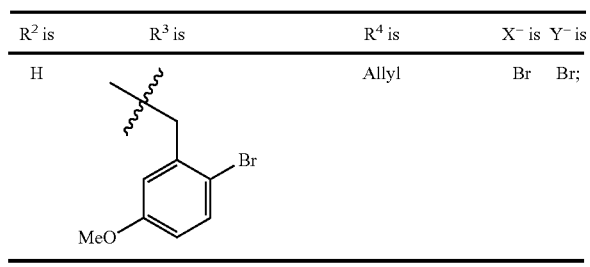 | Br | Br; |
| H | Me | 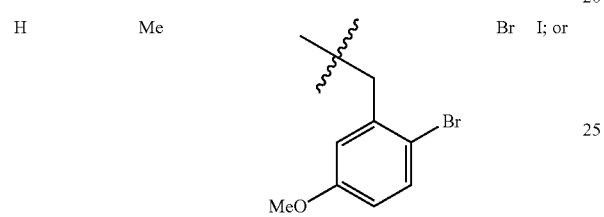 | Br | I; or |
has the structure.
6. The bis-quaternary alkaloid salt of the Formula:
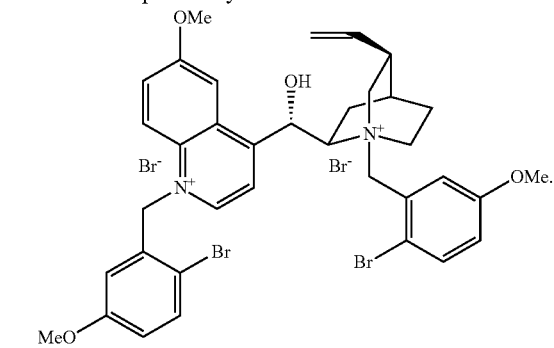
* * * * *